United States Patent [19]

Hansen et al.

[11] Patent Number: 5,693,411

[45] Date of Patent: *Dec. 2, 1997

[54] BINDERS FOR BINDING WATER SOLUBLE PARTICLES TO FIBERS

[75] Inventors: Michael R. Hansen, Seattle; Richard H. Young, Sr., Renton, both of Wash.

[73] Assignee: Weyerhaeuser Company, Federal Way, Wash.

[*] Notice: The term of this patent shall not extend beyond the expiration date of Pat. No. 5,547,745.

[21] Appl. No.: 107,467

[22] Filed: Aug. 17, 1993

Related U.S. Application Data

[63] Continuation-in-part of Ser. No. 931,059, Aug. 17, 1992, Pat. No. 5,543,215, Ser. No. 931,277, Aug. 17, 1992, Pat. No. 5,538,783, Ser. No. 931,213, Aug. 17, 1992, Pat. No. 5,300,192, Ser. No. 931,278, Aug. 17, 1992, Pat. No. 5,352,480, Ser. No. 931,284, Aug. 17, 1992, Pat. No. 5,308,896, and Ser. No. 931,279, Aug. 17, 1992.

[51] Int. Cl.$^6$ .................................................. B32B 5/16
[52] U.S. Cl. ........................ 428/283; 428/288; 428/378
[58] Field of Search .............................. 428/283, 288, 428/375, 378, 393

[56] References Cited

U.S. PATENT DOCUMENTS

| | | |
|---|---|---|
| 2,601,597 | 6/1952 | Daniel, Jr. et al. . |
| 2,953,187 | 9/1960 | Francis, Jr. . |
| 3,010,161 | 11/1961 | Duvall . |
| 3,021,242 | 12/1962 | Touey ............................ 156/180 |
| 3,059,313 | 10/1962 | Harmon ............................ 28/80 |
| 3,070,095 | 12/1962 | Torr ................................ 328/284 |
| 3,087,833 | 4/1963 | Drelich ............................ 117/38 |
| 3,327,708 | 6/1967 | Sokolowski ..................... 128/156 |
| 3,344,789 | 10/1967 | Arnold et al. ................... 128/287 |
| 3,377,302 | 4/1968 | Gugliemelli et al. ............ 260/17.4 |
| 3,395,201 | 7/1968 | Kalwaites ......................... 264/45 |
| 3,425,971 | 2/1969 | Gugliemelli et al. ............ 260/17.4 |
| 3,494,992 | 2/1970 | Wiegand . |
| 3,521,638 | 7/1970 | Parrish ............................. 128/284 |
| 3,554,788 | 1/1971 | Fechillas ......................... 117/140 |
| 3,661,154 | 5/1972 | Torr . |
| 3,661,632 | 5/1972 | Gagliardi et al. ................. 17/143 |
| 3,669,103 | 6/1972 | Harper et al. ................... 128/156 |
| 3,670,731 | 6/1972 | Harmon ........................... 128/284 |

(List continued on next page.)

FOREIGN PATENT DOCUMENTS

| | | |
|---|---|---|
| 729513 | 6/1962 | Canada . |
| 806352 | 4/1964 | Canada . |

(List continued on next page.)

OTHER PUBLICATIONS

Gugliemelli et al., "Base-Hydrolyzed Starch-Polyacrylonitrile (S-PAN) Graft Copolymer. S-PAN-1:1, PAN M.W. 794,000*," J. of Applied Copolymer Science, 13:2007–2017 (1969).

Weaver et al., "Hydrolyzed Starch-Polyacrylonitrile Graft Copolymers: Effect of Structure on Properties*," J. of Applied Polymer Science, 15:3015–3024 (1971).

(List continued on next page.)

Primary Examiner—Christopher Raimund
Attorney, Agent, or Firm—Christensen O'Connor Johnson & Kindness PLLC

[57] ABSTRACT

Improved fibers are provided that may be incorporated into absorbent articles such as disposable diapers, feminine hygiene appliances, and bandages. Water soluble particles are bound to fibrous material by a binder in which the particles are sparingly soluble and which has a volatility less than water. The binder has a functional group capable of forming a hydrogen bond with the fibers, and a functional group that is capable of forming a hydrogen bond or a coordinate covalent bond with the particles. The binder can be activated or reactivated by addition of heat, liquid, or mechanical energy such that fibers treated with binder may be shipped to a distribution point before particles are bound to the fibers.

32 Claims, 6 Drawing Sheets

U.S. PATENT DOCUMENTS

| | | | |
|---|---|---|---|
| 3,672,945 | 6/1972 | Taylor | 117/100 |
| 3,692,622 | 9/1972 | Dunning | 161/124 |
| 3,745,060 | 7/1973 | Jumentier et al. | |
| 3,758,641 | 9/1973 | Zweigle . | |
| 3,766,922 | 10/1973 | Krusko | 128/284 |
| 3,777,758 | 12/1973 | Mesek et al. | 128/284 |
| 3,788,936 | 1/1974 | Brock et al. | 161/148 |
| 3,804,092 | 4/1974 | Tunc | 128/284 |
| 3,808,088 | 4/1974 | Knechtges et al. | 161/148 |
| 3,886,941 | 6/1975 | Duane et al. | 128/287 |
| 3,888,256 | 6/1975 | Studinger | 128/296 |
| 3,888,257 | 6/1975 | Cook et al. | 128/296 |
| 3,901,236 | 8/1975 | Assarsson et al. . | |
| 3,903,889 | 9/1975 | Torr | 128/287 |
| 3,908,659 | 9/1975 | Wehrmeyer et al. | 128/287 |
| 3,923,592 | 12/1975 | George et al. . | |
| 3,949,035 | 4/1976 | Dunning et al. | 264/90 |
| 3,978,257 | 8/1976 | Ring | 428/137 |
| 3,991,237 | 11/1976 | Topfl et al. . | |
| 4,007,083 | 2/1977 | Ring et al. . | |
| 4,009,313 | 2/1977 | Crawford et al. | 428/290 |
| 4,035,217 | 7/1977 | Kennette et al. | 156/279 |
| 4,055,180 | 10/1977 | Karami | 128/287 |
| 4,061,268 | 12/1977 | Demaster . | |
| 4,062,451 | 12/1977 | Gander | 206/524.2 |
| 4,071,636 | 1/1978 | Nishino et al. . | |
| 4,102,340 | 7/1978 | Mesek et al. | 128/287 |
| 4,103,062 | 7/1978 | Aberson et al. | 428/283 |
| 4,160,059 | 7/1979 | Samejima | 428/288 |
| 4,232,674 | 11/1980 | Melican | 128/287 |
| 4,250,660 | 2/1981 | Kitamura et al. . | |
| 4,282,121 | 8/1981 | Goodrich | 206/17.4 |
| 4,287,536 | 9/1981 | Dereser . | |
| 4,289,513 | 9/1981 | Brownhill et al. | 55/387 |
| 4,324,706 | 4/1982 | Tabe et al. . | |
| 4,332,917 | 6/1982 | Heslinga et al. . | |
| 4,338,417 | 7/1982 | Heslinga et al. . | |
| 4,364,992 | 12/1982 | Ito et al. . | |
| 4,379,194 | 4/1983 | Clarke et al. . | |
| 4,394,172 | 7/1983 | Scheuble et al. | 106/38.5 |
| 4,404,250 | 9/1983 | Clarke | 428/220 |
| 4,410,571 | 10/1983 | Korpman | 427/385 |
| 4,412,036 | 10/1983 | Pederson et al. | 525/54.26 |
| 4,424,247 | 1/1984 | Erickson | 427/138 |
| 4,457,978 | 7/1984 | Wawzonek . | |
| 4,467,012 | 8/1984 | Pederson et al. | 428/248 |
| 4,486,501 | 12/1984 | Holbek | 428/375 |
| 4,492,729 | 1/1985 | Bannerman et al. | 428/283 |
| 4,532,176 | 7/1985 | Briggs et al. . | |
| 4,537,767 | 8/1985 | Rothman et al. . | |
| 4,558,091 | 12/1985 | Hubbard | 524/734 |
| 4,597,930 | 7/1986 | Szal | 264/115 |
| 4,673,402 | 6/1987 | Weisman et al. | 604/368 |
| 4,676,784 | 6/1987 | Erdman et al. | 604/368 |
| 4,758,466 | 7/1988 | Dabi et al. | 428/283 |
| 4,772,492 | 9/1988 | Bouchette . | |
| 4,788,080 | 11/1988 | Hojo et al. | 427/204 |
| 4,818,599 | 4/1989 | Marcus . | |
| 4,826,880 | 5/1989 | Lesniak et al. | 521/53 |
| 4,833,011 | 5/1989 | Horimoto | 428/288 |
| 4,842,593 | 6/1989 | Jorden et al. . | |
| 4,874,811 | 10/1989 | Borchers et al. | 524/516 |
| 4,886,697 | 12/1989 | Perdelwitz, Jr. et al. | 428/192 |
| 4,892,769 | 1/1990 | Perdelwitz, Jr. et al. . | |
| 4,902,565 | 2/1990 | Brook . | |
| 5,002,814 | 3/1991 | Knack et al. | 428/85 |
| 5,057,166 | 10/1991 | Young, Sr. et al. | 156/62.2 |
| 5,064,689 | 11/1991 | Young, Sr. et al. . | |
| 5,128,082 | 7/1992 | Makoui | 264/112 |
| 5,161,686 | 11/1992 | Weber et al. | 206/440 |
| 5,217,445 | 6/1993 | Young et al. . | |
| 5,225,047 | 7/1993 | Graef et al. . | |
| 5,230,959 | 7/1993 | Young, Sr. et al. . | |
| 5,252,275 | 10/1993 | Sultze et al. . | |
| 5,252,340 | 10/1993 | Honeycutt . | |
| 5,278,222 | 1/1994 | Stack . | |
| 5,283,123 | 2/1994 | Carter et al. . | |
| 5,300,054 | 4/1994 | Feist et al. . | |
| 5,300,192 | 4/1994 | Hansen et al. . | |
| 5,308,896 | 5/1994 | Hansen et al. . | |
| 5,312,522 | 5/1994 | Van Phan et al. . | |
| 5,352,480 | 10/1994 | Hansen et al. . | |
| 5,362,776 | 11/1994 | Barenberg et al. . | |
| 5,432,000 | 7/1995 | Young, Sr. et al. | 428/372 |
| 5,447,977 | 9/1995 | Hansen et al. . | |

FOREIGN PATENT DOCUMENTS

| | | |
|---|---|---|
| 813616 | 12/1965 | Canada . |
| 841940 | 12/1965 | Canada . |
| 953 890 | 9/1974 | Canada . |
| 1052156 | 12/1976 | Canada . |
| 0 071 063 A1 | 2/1983 | European Pat. Off. . |
| 0 096 976 A2 | 12/1983 | European Pat. Off. . |
| 122042 | 10/1984 | European Pat. Off. . |
| 0 210 754 A1 | 2/1987 | European Pat. Off. . |
| 0 427 316 A2 | 7/1989 | European Pat. Off. . |
| 0 427 317 A2 | 7/1989 | European Pat. Off. . |
| 0 429 112 A2 | 7/1989 | European Pat. Off. . |
| 0 440 472 A1 | 1/1990 | European Pat. Off. . |
| 0 442 185 A1 | 8/1991 | European Pat. Off. . |
| 0 509 708 A1 | 10/1992 | European Pat. Off. . |
| 1 382 716 | 1/1964 | France . |
| 1 382 716 | 2/1964 | France . |
| 489 308 | 1/1930 | Germany . |
| 1 079 796 | 6/1962 | Germany . |
| 2 048 721 | 6/1971 | Germany . |
| 29 49 531 A1 | 7/1980 | Germany . |
| 61-28422 | 2/1986 | Japan . |
| 1 217 452 | 12/1969 | United Kingdom . |
| 2 007 998 A | 5/1979 | United Kingdom . |
| 2 092 895 A | 8/1982 | United Kingdom . |
| 2189127 | 10/1987 | United Kingdom . |
| WO 88/01316 | 2/1988 | WIPO . |
| WO 90/09236 | 8/1990 | WIPO . |
| WO 90/11181 | 10/1990 | WIPO . |
| WO 93/24153 | 12/1993 | WIPO . |
| WO 94/04351 | 3/1994 | WIPO . |
| WO 94/04352 | 3/1994 | WIPO . |
| WO 95/00703 | 1/1995 | WIPO . |

OTHER PUBLICATIONS

Weaver et al., "Highly Absorbent Starch–Based Polymer," Northern Regional Research Laboratory, Agricultural Research Service, U.S. Dept. of Agriculture, Peoria, Illinois, pp. 169–177.

"Super slurpers: Time for change?," Chemical Week, pp. 21–22 (Jul. 24, 1974).

S. Lammie, "Use of Glycerine as a Softener for Paper Products," The World's Paper Trade Review, Dec. 13, 1962, p. 2050.

Lindsay, "Absorbent Starch Based Co–polymers—Their Characteristics and Applications," Formed Fabrics Industry, pp. 20, 24 and 26 (May 1977).

Burkholder, "Absorbent Polymers—A New Concept in Fluid Absorption," The Dow Chemical Company Designed Products Laboratory, Midland, Michigan, pp. 73–79 (1973).

Lysogorskaya et al., "Effect of Moisture Content on the Development of Interfiber Bonds in Air-Laid Paper," Leningrad Technological Institute of the Pulp and Paper Industry, Zh. Prikl. Khim., 63:(8) 1869–1872 (1990).

Ogurtsov et al., "Effect of the modulus of elasticity of the binder on the properties of dry-process paper," Sb. Tr. Tsentr. Nauch.–Issled. Inst. Bumagi, 9:123–127 (1974).

Amosov et al., "Aluminum hydroxy compounds—binders for dry-process paper," Izv. VUZ, Lesnoi Zh., 6:72–76 (1986).

Gorbushin et al., "Investigation of the effect of the nature and concentration of binders on the properties of dry-process paper," Sb. Tr. Tsentr. Nauch.–Issled. Inst. Bumagi, 9:117–123 (1974).

Hoque et al., "Granulation and Tabletting of Iron Oxide–Chromic Oxide Catalyst Mass with the Aid of Binding Ingredients Part II–Cellulosic Derivatives and Polyethylene Glycol as Binding Ingredients," Fertilizer Technology, 20:30–35 (1983).

Lysogorskaya et al., "Effect of Moisture Content on Development of Interfiber Bonding in the Structure of Air–Dried Paper," Plenum Publ. Corp., pp. 1730–1733 (1991).

Sliwiok and Kowalska, "Investigation of Self–Association of the Selected Glycols and Cellulose Sorbents," Microchemical Journal, 26:68–74 (1981).

Blanchard and Reinhart, "Dyeing of Crosslinked Cotton Containing Glycol Additives," U.S. Dept. of Agriculture, New Orleans, 24:13–17 (Jan. 1992).

Byrd, "How bonds develop during web consolidation," PTI, pp. 240–243 (Oct. 1986).

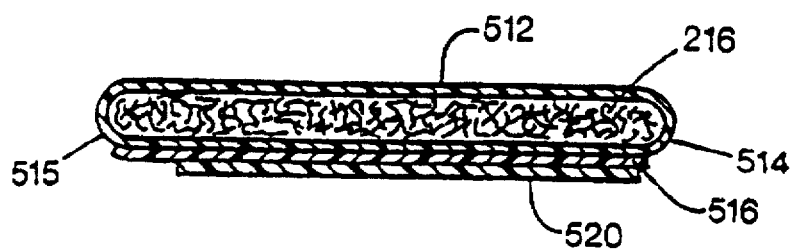
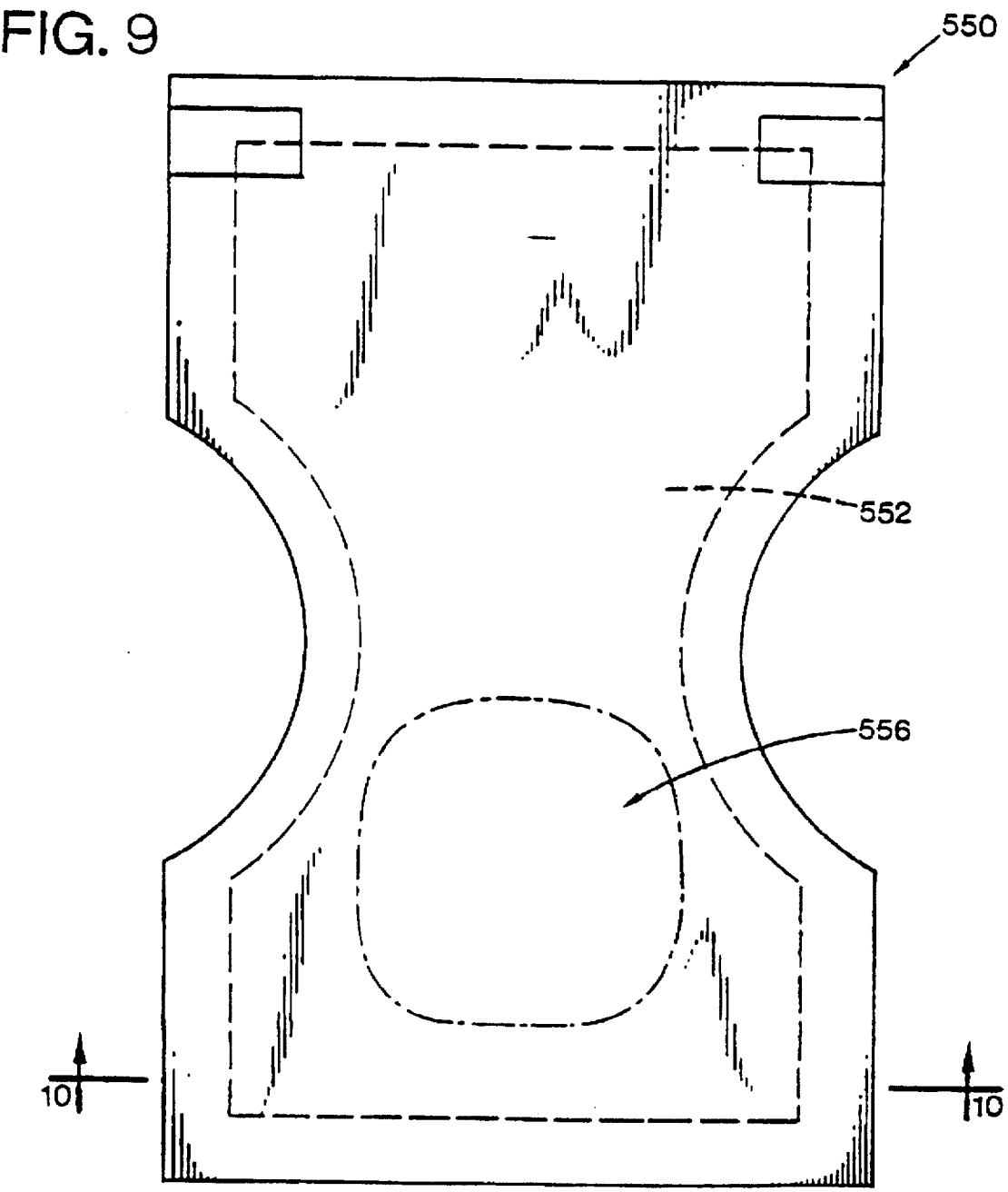

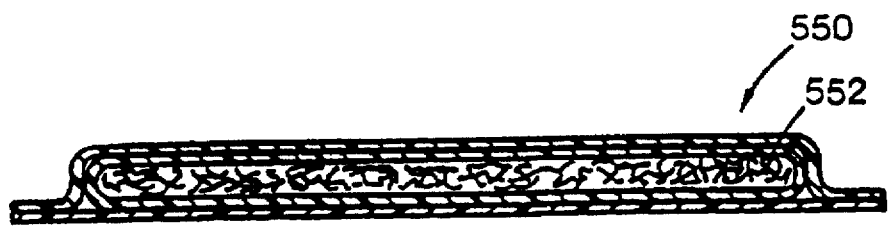
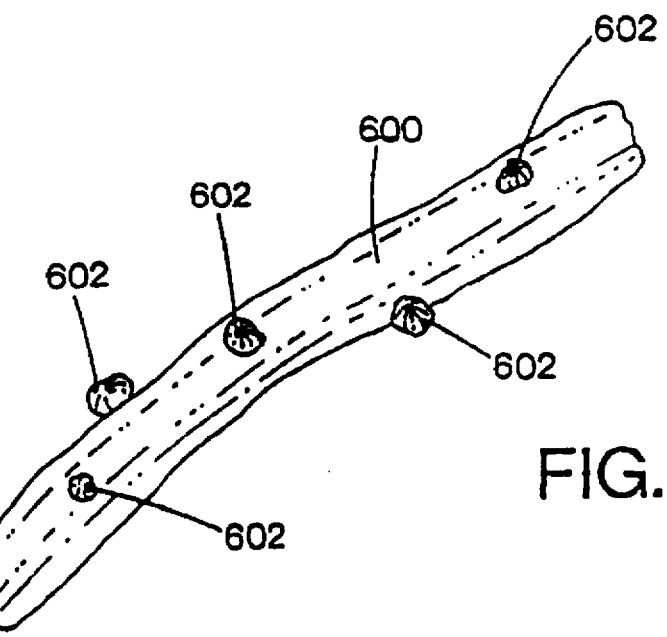
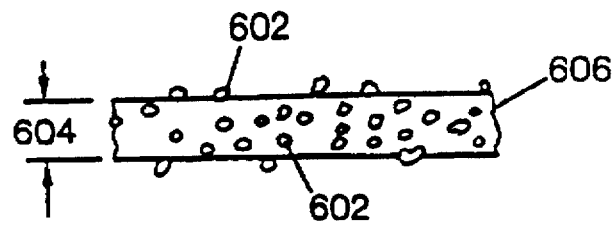

BINDERS FOR BINDING WATER SOLUBLE PARTICLES TO FIBERS

CROSS REFERENCE TO RELATED APPLICATIONS

This is a continuation-in-part application of the following U.S. patent applications, each of which was filed on Aug. 17, 1992, and each of which is hereby incorporated herein by reference: (1) Ser. No. 07/931,059, entitled "POLYMERIC BINDERS FOR BINDING PARTICLES TO FIBERS" now U.S. Pat. No. 5,543,215; (2) Ser. No. 07/931,277, entitled "NON-POLYMERIC ORGANIC BINDERS FOR BINDING PARTICLES TO FIBERS" now U.S. Pat. No. 5,538,783; (3) Ser. No. 07/931,213, entitled "WET LAID FIBER SHEET MANUFACTURING WITH REACTIVATABLE BINDERS FOR BINDING PARTICLES TO BINDERS" now U.S. Pat. No. 5,310,192; (4) Ser. No. 07/931,278, entitled "REACTIVATABLE BINDERS FOR BINDING PARTICLES TO FIBERS" now U.S. Pat. No. 5,352,480; (5) Ser. No. 07/931,284, entitled "PARTICLE BINDERS FOR HIGH BULK FIBERS" now U.S. Pat. No. 5,308,896; and (6) Ser. No. 07/931,279, entitled "PARTICLE BINDERS THAT ENHANCE FIBER DENSIFICATION pending."

FIELD OF THE INVENTION

This invention concerns polymeric and non-polymeric binders for fibers and the use of such binders in binding water soluble particles to fibers. In particular embodiments, it concerns binding such particles to cellulosic fibers which may then be used, for example, to make fibers that are incorporated into absorbent articles.

BACKGROUND OF THE INVENTION

One problem with the use of solid particles in cellulosic products is that the particulate material can be physically dislodged from the cellulosic fibers of an absorbent product. Separation of the particle from its substrate reduces the desired properties of the product. The problem of particulate separation was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. No. 4,412,036 and U.S. Pat. No. 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. No. 2,757,150; U.S. Pat. No. 4,584,357; and U.S. Pat. No. 4,600,462. Such binders are not described as being useful in binding particulates to fibers. Yet other patents disclose crosslinking agents such as polycarboxylic acids that form covalent intrafiber bonds with individualized cellulose fibers, as in European Patent Application 440472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker. The covalent bonds between the fibers produce a pulp sheet that is more difficult to compress to conventional pulp sheet densities than in an untreated sheet. Any covalent crosslink bonds that form between the fibers and particles occupy functional groups that would otherwise be available for absorption, hence absorption efficiency is decreased.

Many different types of particles may be added to fibers for different end uses. Antimicrobials, zeolites and fire retardants are but a few examples of particles that are added to fibers. It would be advantageous to provide a method of attaching particles that could be accommodated to the many different particle needs of end users. Moreover, it would be advantageous to reduce particulate waste in the attachment process, and simplify shipment of fiber products that require particulate addition.

It has previously been important that particles added to cellulose products be insoluble in liquids such as water or liquid binders. It has been thought that liquid insolubility (particularly water insolubility) was an essential characteristic for particles bound to cellulose fibers because soluble particles would be dissolved by a water containing binder. Although the particle could eventually resolidify as the binder evaporated, dissolution of the particle in the binder would cause the particle to diffuse to areas of the product where it was not needed or desired.

Accordingly, it is an object of this invention to provide an improved method of binding water soluble particulates to fibers.

Another object of the invention is to provide an improved method which can be customized to easily allow different end users of the products to bind different kinds of water soluble particles to the fibers.

It is another object to provide an improved method of binding water soluble particulates such that they can be distributed throughout a fibrous product in a desired distribution, particularly in a discrete segregated region of a product, and without necessarily being confined to the surface of a product.

Another object of the invention is to provide improved fiber and absorbent products in which water soluble particulates are firmly bound to cellulose fibers such that the particles are less likely dislodged by mechanical forces.

Yet another object of the invention is to provide binders for water soluble particles which are environmentally compatible and more easily biodegradable.

Finally, it is an object of the invention to bind a broad variety of water soluble particles to many different kinds of fibers using an improved, simple and versatile binding process that limits particle waste.

SUMMARY OF THE INVENTION

The foregoing and other objects are achieved by providing fibers with hydrogen bonding functional sites, adding and applying to the fibers a binder that has a volatility less than water. The water soluble particles may then be added to the binder and fibers. Also, the water soluble particles may be mixed with fibers, and a binder thereafter applied to the particles and fibers. The binder comprises binder molecules. The binder molecules have at least one functional group that is capable of forming a hydrogen bond with the fibers, and at least one other functional group that also is capable of forming a hydrogen bond or a coordinate covalent bond with water soluble particles which also have a like hydrogen bonding or coordinate covalent bonding functionality. The binder attaches the water soluble particles to the fibers, and forms a bond with both the fiber and the particle that has been found to be resistant to mechanical disruption. This particle attachment can be accomplished at the time and place the binder is applied or subsequently at the same or at a remote location. A significant advantage of these binders is that the binders can optionally be present on fibers, in an inactive state. The inactive binder is then later activated or reactivated to bind water soluble particles to the fibers. For purposes of this description, activation will hereinafter be used to include both initial activation of a binder (e.g. of a solid binder) to attach particles as well as reactivation of a binder (e.g. applying liquid to or otherwise treating a binder that initially could adhere particles but which was allowed to go to an inactive state (e.g. to dry) where it no longer adheres particles) so as to adhere particles. The particles are soluble in water but have reduced solubility in the binder such that the particles can be bound in solid particulate form to the fibers. Addition of the binder does not dissolve the particle and cause it to diffuse away from its desired site of attachment to the fibers.

Liquid binders (which include aqueous solutions of solid binders or neat liquids) can be placed on the fibers, air dried, and later activated. A dry solid binder may be added to the fibers and later activated by addition of a liquid, such as by spraying or fogging the activating liquid onto the fibers. An inactive binder also can be activated by applying kinetic energy to a mixture of fibers and binder, for example, after the binder and fibers reach an equilibrium moisture content with the atmosphere (hereinafter referred to as "air drying"). Kinetic energy can be applied to the fibers, for example, by mechanically agitating the binder and fibers. In yet other embodiments, the binder may be activated by heating the fibers after applying the binder to the fibers.

The capacity for activation allows the binder to be applied to the fibers, which are then shipped to remote locations such as distribution points with the binder in an inactive form. The binder may then be activated at the distribution point or remote location where particles are added to the fibers and bound thereto. The binder then can be activated at the remote location. Again, as used herein, binder "activation" includes both activation of previously inactive binders (such as solid binders in the absence of liquid) or activation of previously active binders (such as a liquid binder that has been dried).

Another advantage of the present invention is that the binder can be activated in a pattern that corresponds to a desired distribution of particles in fibrous material. An activating fluid, such as a liquid, for example water or one of the binders of the present invention, can be applied to target areas of an article, such as the crotch area of a diaper that will be initially moistened by urine during use. Water soluble particles can be added to the activated area of the diaper and adhered almost exclusively in those areas where initial urine absorption is required. Targeted activation of binder allows such particles to be efficiently and economically attached to the fibers, with reduced particle wastage. Moreover, targeted binder activation and water soluble particle adherence increases the efficiency of the product by concentrating the particles at locations where they are most useful.

The fibers of the present invention may have water soluble particles bound to the fibers with a polymeric or a non-polymeric binder.

The polymeric binder may be selected from the group consisting of polyglycols [especially poly(propyleneglycol)], a polycarboxylic acid, a polycarboxylate, a poly(lactone) polyol, such as diols, a polyamide, a polyamine, a polysulfonic acid, a polysulfonate and combinations thereof. Specific examples of some of these binders, without limitation, are as follows: polyglycols include polypropylene glycol (PPG), polyethylene glycol (PEG), and polyglycerol; poly (lactone) polyols include poly(caprolactone) diol and poly (caprolactone) triol;. polycarboxylic acid include polyacrylic acid (PAA); polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid); and copolymers thereof (for example a polypropylene glycol/ polyethylene glycol copolymer). The polymeric binder typically has repeating units. The repeating unit may be the backbone of a compound, such as with a polypeptide, wherein the repeating polyamides occur in the peptide chain. The repeating unit may also refer to units other than backbones, for instance a repeating acrylic acid unit. In such a case, the repeating units may be the same or different. Each binder molecule has at least one functional group capable of forming a hydrogen bond or a coordinate covalent bond with particles, and at least one hydrogen bond with the fibers. At this time, the most preferred polymeric binder is polyethylene glycol although another especially preferred polymeric binder is an amide binder such as a polypeptide with polyglycines being a specifically preferred example.

The non-polymeric binder has a volatility less than water, a functional group that is capable of forming hydrogen bonds or coordinate covalent bonds with the particles, and a functional group that is capable of forming hydrogen bonds with the cellulose fibers. The non-polymeric binder is an organic binder, and preferably includes a functional group selected from the group consisting of a carboxyl (for example, carboxylic acids), a carbonyl (for example, aldehydes), a sulfonic, a sulfonate, a phosphoric acid, a phosphate, a hydroxy acid, a hydroxyl, an alcohol, an amide, an amine, and combinations thereof (for example, amino acid), wherein there are at least two functionalities on the molecule selected from this group, and the two functionalities are the same or different. Examples of such binders include polyols, polyamines (a non-polymeric organic binder with more than one amine group), polyamides (a non-polymeric organic binder with more than one amide group), polycarboxylic acids (a non-polymeric organic binder with more than one carboxylic acid functionality), polyaldehydes (a non-polymeric organic binder with more than one aldehyde), amino alcohols, hydroxy acids and other binders. These binders have functional groups that are capable of forming the specified bonds with the particles and fibers.

More preferably, the organic non-polymeric binder is selected from the group consisting of glycerin, a glycerin monoester, a glycerin diester, a polyglycerin oligomer, glyoxal, ascorbic acid, urea, glycine, pentaerythritol, a monosaccharide or a disaccharide, citric acid, tartaric acid, taurine (2-aminoethanesulfonic acid), p-aminosalicylic acid dipropylene glycol, and urea derivatives such as DMDHEU and combinations thereof. Suitable saccharides include glucose, sucrose, lactose, ribose, fructose, mannose, arabinose, and erythrose. The preferred binders are non-polymeric molecules with a plurality of hydrogen bonding functionalities that permit the binder to form hydrogen bonds to both the fibers and particles. Particularly preferred binders include those that can form five or six membered rings, most preferably six membered rings, with a functional group on the particle surface. At present, glycerin, glycerin monoesters, glycerin diesters, polyglycerol oligomers, and blends of these with urea are the preferred binders. At this time, specifically preferred non-polymeric binders are glycerin and glycerin urea blends. When the binder is glycerin it binds only particles to the fibers without substantial fiber to fiber bonding.

The fibrous material may be cellulosic or synthetic fibers that are capable of forming hydrogen bonds with the binder, while the water soluble particles are capable of forming hydrogen bonds or coordinate covalent bonds with the binder. This binder system secures these particles to fibers unexpectedly well. A superior fibrous product is therefore produced that has improved properties as compared to products with unbound or covalently bound particles. Formation of the noncovalent bond allows production of a fiber product that is easily manufactured and a web that is easily densified, and that is readily biodegradable and disposable.

In one preferred embodiment, an absorbent product comprises a fibrous cellulosic mat that contains water soluble particles in particulate form. The particles are capable of forming hydrogen bonds or coordinate covalent bonds with the binder, depending upon the binder, while the binder in turn is capable of forming hydrogen bonds with the hydroxyl groups of the cellulose fibers. These noncovalent, relatively flexible bonds between the binder and particles maintain the particles in contact with the fibers, and resist dislodgment of the particles by mechanical forces applied to the mat during manufacture, storage or use. The particles have low solubility in the binder. The binder may suitably be present in an amount of from about 1 to 80 percent, more preferably 3 to 60 percent, of the total weight of the fibrous material, while the particles bound to the binder of the present invention (via hydrogen/coordinate covalent bonds) may be suitably present in an amount of 0.05 to 80 percent of the total weight of the fibrous material and particles, preferably 1 to 80 percent or 5 to 80 percent by weight or more than 5 percent by weight. An especially suitable range of binder is 3 to 40 percent by weight of the fibrous material, or 3 to 25 percent by weight, while a particularly suitable range of such particles is 5 to 40 percent by weight of the fibrous material and particles. A preferred weight ratio of particle to binder is 2:1 to 10:1. For antimicrobials and some other particles, lower weight ratios may be preferred, for example, chlorhexidine digluconate (solubility in water greater than 50%) may be present in less than 0.2% by weight of the product. An example of suitable particles are sodium bicarbonate, ethylenediaminetetraacetic acid, oxalic acid, or aluminum sulfate, which are capable of forming hydrogen bonds or coordinate covalent bonds with the binder. The binder is also capable of forming hydrogen bonds with the hydroxyl groups of the cellulose, thereby securely attaching the particles to the fibers.

Other particles may be adhered to the fibers in combination with the water soluble particles. Preferably, although not necessarily, those other particles have the same functionality as the water soluble particles so that they too will be strongly bound. An example is superabsorbent polymer such as a starch graft polyacrylate hydrogel fine or larger size particle such as a granule, which forms hydrogen bonds with the binder. The binder also forms hydrogen bonds with the hydroxyl groups of the cellulose, thereby securely attaching the superabsorbent particles to the fibers.

In especially preferred embodiments, the fibers are cellulosic and the particles are bound to the binder by hydrogen bonds. The fibers may also be continuous or discontinuous synthetic or natural fibers having a hydrogen bonding functional group that hydrogen bonds with the binder. The water soluble particles may be bound to the fibers at less than 150° C., or without any external application of heat at ambient temperature (e.g., about 25° C.). Water soluble particles may also be bound in the absence of any external application of pressure, or in the absence of external heat and pressure.

In some embodiments the binder is associated with the fibers as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin or a solution of glycine powder), the fibers suitably contain at least about 0.5 percent water by weight. A solid binder is suitably used with fibers having less than 0.5 percent water by weight if the binder is heated above its melting point to liquefy it. In such a case, the solid can be applied to the fibers as a supersaturated solution or the solid binder may be heated above its melting point and applied to the fibers. Upon solidifying the binder is deactivated. A solid binder may be thermoplastic or meltable, such that it can be heated above its melting point and then cooled to fuse fibers to each other. The thermoplastic properties of the binder can also provide additional mechanical adherence between the particles and fibers. In some embodiments, a meltable binder such as urea may be employed which can adhere particles both physically and with hydrogen bonding.

NMR studies indicate that the functional groups are not only capable of forming hydrogen bonds with the fibers and hydrogen bonds or coordinate covalent bonds with the particles but do form such bonds.

The invention also includes the fibrous products produced by any of the methods described herein, and further includes products in which fibers have the disclosed binders associated with or applied to the fibers, with the water soluble particles adhered to the fibers. The invention also relates to absorbent products or articles comprised of such fibrous products. These fibrous products include fibers with inactive or activatable binders.

The present invention relates to the above objects, advantages and features individually as well as collectively. The foregoing and other features and advantages of the invention will become more apparent from the following detailed description and accompanying drawings.

BRIEF DESCRIPTION OF THE DRAWINGS

FIG. 8 is a sectional view of the appliance of FIG. 9 taken along line 8—8 of FIG. 7.

FIG. 9 is a plan view of a disposable diaper including a core of fibers of the present invention.

FIG. 10 is a vertical sectional view of the diaper of FIG. 9.

FIG. 11 is a view of an enlarged fiber with particles bonded to the fiber with the binders of the present invention.

FIG. 12 is a schematic view of a cellulose mat with particles bound to all its surfaces and throughout its depth.

DETAILED DESCRIPTION OF SEVERAL PREFERRED EMBODIMENTS OF THE INVENTION

Fiber Characteristics

Figure 1:
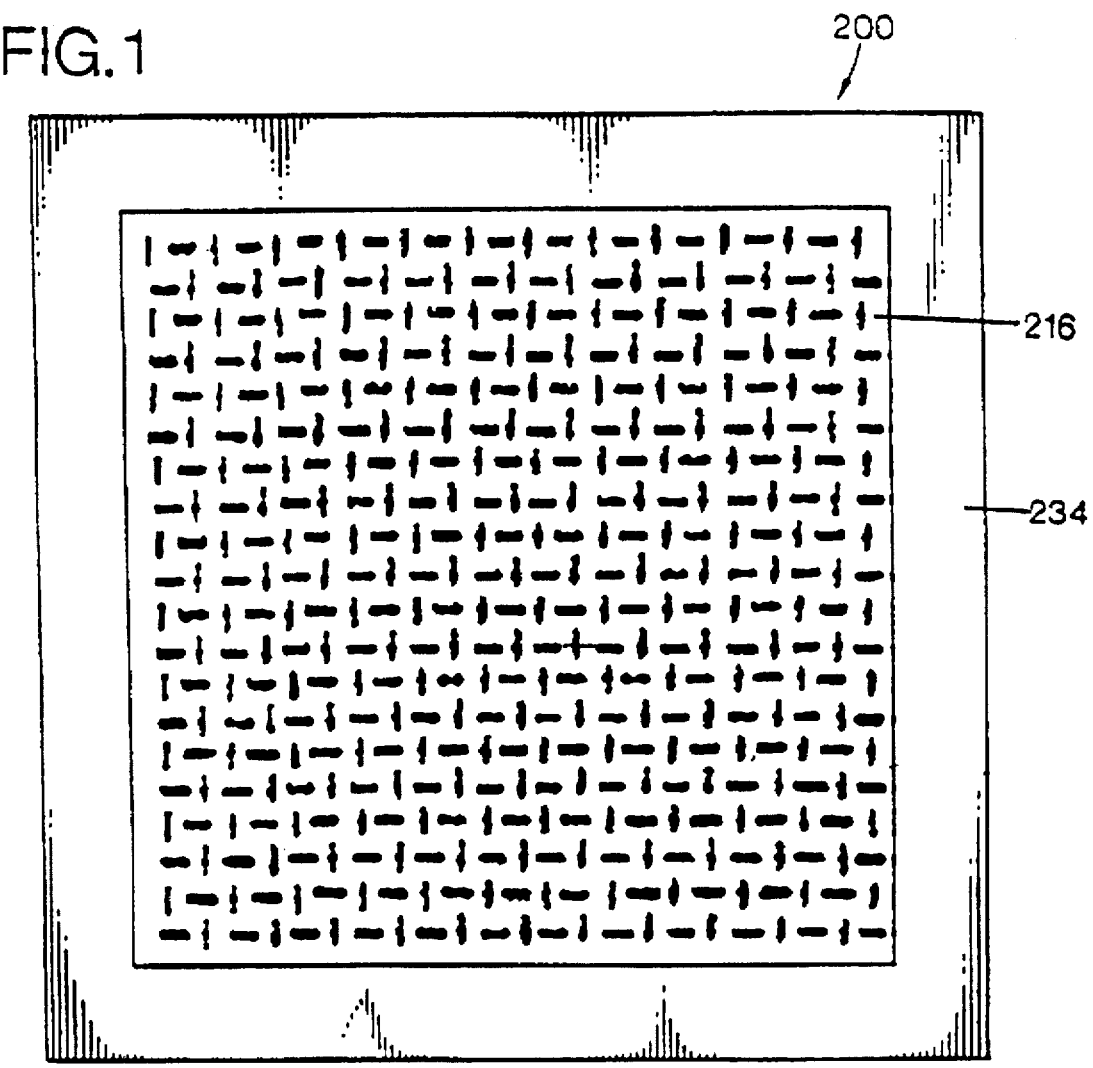
FIG. 1 is a top plan view of an absorbent article or structure into which fibers of the present invention are incorporated with attached particles, the fibers being in the form of an illustrated absorbent pad.

The present invention includes a method of binding water soluble particles to fibers, and further includes fibers with disclosed binders and products, including absorbent end products or articles made therefrom. In particularly preferred embodiments, the product is a cellulosic or synthetic fiber to which water soluble particles are adhered by a binder, and absorbent products made therefrom. Other non-water soluble particles may also be adhered to the fibers in combination with the water soluble particles. The invention also includes a combination of wood pulp and certain binders, which for the purpose of this combination are bulk fibers in roll form having a basis weight of at least 350 grams per square meter ($g/m^2$) or bale form. The bulk fibers can have a density of at least about 400 $kg/m^3$. Preferred bulk fibers are wood pulp fibers or softwood pulp fibers. The pulp fibers may be chemical or thermomechanical or chemithermomechanical or combinations thereof. The preferred pulp fiber is chemical. Suitable fibers include wood pulp fibers, which can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio greater than about 5:1.

The fibers of the present invention also include fibers that are pretreated prior to the application of a binder to the fibers as explained below. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers may also be pretreated in a way which increases their wettability. For example, natural fibers may be pretreated with a liquid sodium silicate, as by spraying the fibers with this material, for pretreatment purposes. Wettability of the surface of fibers is also improved by subjecting the fibers to a corona discharge pretreatment in which electrical current is discharged through the fibers in a conventional manner. In the case of both synthetic fibers and wood pulp fibers, corona discharge pretreatment results in an oxygen functionality on the surface of the fibers, making them more wettable and more bondable. The fibers may also be pretreated with conventional cross-linking materials and may be twisted or crimped, as desired. Pretreating cellulose fibers with chemicals which result in lignin or cellulose rich fiber surfaces may also be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, one can use antimicrobial solutions (such as solutions of antimicrobial particles as set forth below), as well as solutions of fertilizers and pesticides, and/or fragrances and flavors, for release over time during the life of the fibers. Fibers pretreated with other chemicals, such as thermoplastic and thermoset resins may also be used. Combinations of pretreatments may also be employed with the resulting pretreated fibers then being subjected to the application of the binder coating as explained below.

Ground wood fibers, recycled or secondary wood pulp fibers, and bleached and unbleached wood pulp fibers can be used. Details of the production of wood pulp fibers are well known to those skilled in the art. These fibers are commercially available from a number of companies, including Weyerhaeuser Company, the assignee of the present invention.

The fibers can also be any of a variety of other natural or synthetic fibers, however, all of the fibers to which water soluble particles are attached in accordance with the present invention include a hydrogen bonding functionality. This does not preclude the blending of such fibers with fibers lacking this characteristic. However, the fibers lacking a hydrogen bonding functionality will not have particles bonded thereto with the strength and manner of the bonds that would be present if the fibers had a hydrogen bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen bonding functionality is a functional group that contains an oxygen or nitrogen atom, for example hydroxyls, carboxyls, sulfonic acids, sulfoamides, ethers, esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The 1s orbital of hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon and nylon. The hydrogen bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle to fiber bonding in the manner of the present invention because they include only carbons and hydrogens without any oxygens or nitrogens that can participate in hydrogen bonds.

For purposes of convenience, and not to be construed as a limitation, the following description proceeds with reference to the treatment of individual chemical wood pulp fibers. The fibers are individualized, for example by defiberization in a hammermill. Such individualized fibers are conventionally formed into a mat, and are commercially available, for example as NB 416 fibers from the Weyerhaeuser Company. Another suitable cellulosic mat would include Rayfloc JLD from ITT Rayonier. The cellulose fibers may be in the form of a cellulosic web or loose cellulose fibers.

Water Soluble Particle Characteristics

In accordance with the present invention, particles are added to the fibers to give the fibers desired properties, such as, by way of example only, odor absorbency, pH modification, hemostasis, or antimicrobial activity. The particles adhered to the fibers in accordance with the present invention can be any water soluble particulate material that has limited solubility in the binder, has the desired property, and which is capable of forming hydrogen bonds or coordinate covalent bonds with the binder. Hydrogen bonds can be formed, as discussed above, by particles that contain functional groups having an oxygen or nitrogen. Coordinate covalent bonds, in contrast, are formed by donation of a lone pair of electrons on one atom to an empty orbital of another atom. Coordinate covalent bonds differ from covalent bonds in that covalent bonds are formed by a pair of electrons wherein one of the electrons is donated from each of the atoms that participate in the bond. Water soluble particles can form coordinate covalent bonds if they have an empty p or d or f orbital that is capable of accepting a pair of electrons from the binder. Water soluble particles may also be blended with other particles having these characteristics. Particles without these characteristics may also be included, but they do not strongly bond in the same way as particles with these characteristics.

A coordinate covalent bond occurs between a donor atom that has a lone pair of electrons to donate to the bond, and an acceptor atom that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be. However, metals in periods less than 3 do not have sufficient affinity for electrons to participate in coordinate covalent bonding. Beginning with column IIIB (boron), the three p orbitals participate in coordinate covalent bonding and the lobes of the p orbitals begin to fill. Boron has one electron in one of the 2p orbitals, thus leaving the other 2p orbitals empty and available for coordinate covalent bonding. An example of a coordinate covalently bonded boron containing particle is boric acid, which is used as an astringent, antiseptic and fire retardant. Boric acid is shown below wherein the boron is coordinate covalently bonded to a polypropylene glycol (PPG) binder. This is a hypothetical example illustrating the principles of coordinate covalent bonding even though this is not representative of aqueous boron chemistry. Moreover, the bonding mechanism shown below may not be the bonding mechanism that occurs when practicing the present invention. This hypothetical example is provided merely to illustrate one possible mechanism for coordinate covalent bonding that is believed to occur when practicing the present invention.

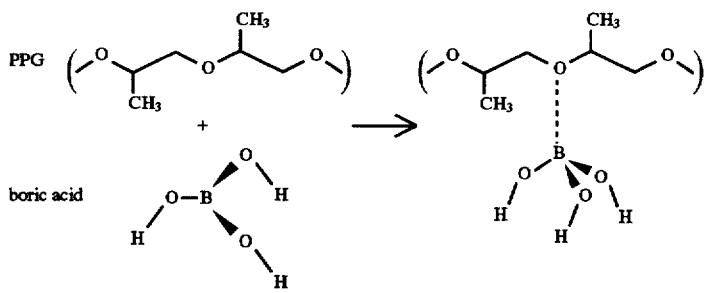

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium, but these metals in groups IA and IIA do not form coordinate covalent bonds as discussed above. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron pair donor to form a coordinate covalent bond. An example of this is found in the bonding in $PCl_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

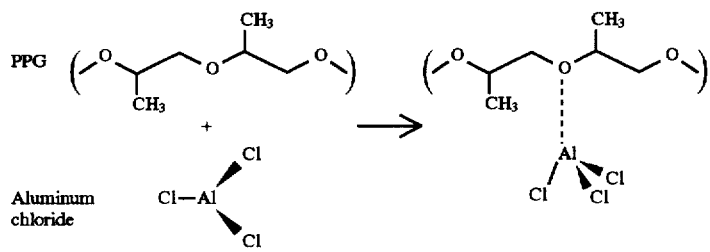

wherein aluminum chloride is coordinate covalently bonded to a polypropylene glycol (PPG) polymer. In this example, the aluminum atom of aluminum trihydrate acts as an electron acceptor for an electron pair donated by an oxygen atom of the polypropylene glycol (PPG) binder. This is a hypothetical example illustrating the principles of coordinate covalent bonding, even though this may not be representative of aqueous aluminum chemistry.

In the next row, the 4s orbital is filled first, then the 3d lobes begin to fill—one electron per lobe until all have a single then a second electron to each lobe until all lobes are filled. However, 4p and 4f orbitals are also available, hence many of the transition elements are capable of forming coordinate covalent bonds.

The elements that have empty orbitals that participate in coordinate covalent bonding include all those except the metals (which excludes hydrogen) in periods one and two, and C, N, O, F, Ne and He. Especially preferred particles contain boron, aluminum, iron, rhodium, osmium, platinum, and palladium, and most particularly boron. Examples of particles that are capable of coordinate covalent bonding, are of limited solubility in the binder, and yet are water soluble are: aluminum chloride ($AlCl_3$), ferric albuminate, ferric chloride, ferric formate, and manganese acetate. All of the polymeric binders of the present invention (PPG, PAA, poly(caprolactone) diol, polyamide and polyamine, etc.) are capable of donating a lone pair of electrons from an oxygen or nitrogen to form a coordinate covalent bond with a suitable particle that has an empty orbital for coordinate covalent bonding.

Suitable Particles

Many water soluble particles that form hydrogen bonds or coordinate covalent bonds are suitable for use with the binders of the present invention. Some such particles are listed in Table 1 with an indication of the function of the listed particles.

TABLE I

| Particulates For Binding | |
|---|---|
| Name | Function |
| Ethylenediaminetetraacetic acid (EDTA) | Odor absorbent |
| disodium salt of EDTA | Chelator |
| Sodium bicarbonate modifier | Odor absorbent/pH |
| Acarbose | Antidiabetic |
| Acefylline Piperazine | Bronchodilator |
| Acenocoumarol, sodium salt | Anticoagulant |
| Acephate | Insecticide |

TABLE I-continued

| Particulates For Binding | |
|---|---|
| Name | Function |
| Acetaminophen | Analgesic |
| Acetylleucine | Antivertigo agent |
| Monoethanolamine | |
| Acid Violet 7B | Dye/Stain |
| Acitretin | Antipsoriatic |
| Acranil | Antiprotozoal (Giardia) |
| Acriflavine | Anti-infective |
| Actaplanins | Growth stimulant |
| Algestone Acetophenide | Antiacne |
| Algin | Hemostatic |
| Almagate | Antacid |
| (−)-Ambroxide | Fragrance |
| Ambucaine hydrochloride | Local anesthetic |
| Amodiaquin | Antimalarial |
| Anabasine hydrochloride | Insecticide |
| o-Anisaldehyde | Fragrance |
| Anisomycin hydrochloride | Topical antitrichomonal |
| Aralkonium chloride | Antiseptic, germicide |
| Asiaticoside | Dermatide, wounds, burns |
| Aspartame | Non-nutritive sweetener |
| Azidoamphenicol | Antimicrobial in eye infections |
| Bebeerine | Antimalarial |
| Potassium benzoate | Preservative, antifungal |
| Benzoyl peroxide | Dermatide, antiacne |
| Benzylidene acetone | Fragrance |
| Bidrin | Insecticide |
| Biphenamine hydrochloride | Antiseborrheic |
| Bishydroxycoumarin | Anticoagulant |
| Bismuth tribromophenate | Topical antiseptic |
| Blasticidin S hydrochloride | Antimicrobial |
| Bromocresyl green | Indicator |
| Bromophenol blue | Indicator |
| Butathamine hydrochloride | Anesthetic |
| Caffeine hydrochloride | CNS Stimulant |
| Calcium ascorbate | Vitamin C/Calcium source |
| Calcium bisulfite | Germicide |
| Calcium thioglycollate | Depilatory |
| Carbachol | Ophthalmic parasympathomimetic |
| Carbowax | Ointment base |
| Cetalkonium chloride | Antibacterial |
| Cethoxonium bromide | Antiseptic |
| Chartreusin | Antimycobacterial |
| Chloramine-T | Topical antiseptic |
| Cinnamic acid | Fragrance |
| Cotamine chloride | Hemostatic |
| Demercarium bromide | Topical antiglaucoma |
| D-2-deoxyribose | DNA synthesis |
| Dequalinium chloride | Antiseptic |
| Dermostatin | Anti fungal |
| Dexamethasone | Glucocorticoid |
| Diacetone acrylamide | Mfr coatings, adhesives |
| 2,4-Diamino-6-hydroxypyrimidine | Indicator of nitrates/nitrites |
| 2,4-Diaminophenol | Photographic |

TABLE I-continued

Particulates For Binding

| Name | Function |
|---|---|
| dihydrochloride | developer |
| Diamthazole dihydrochloride | Antifungal |
| Diatrizoate sodium | Diagnostic aid |
| Dibekacin sulfate | Antibacterial |
| Disodium 4',5'-dibromofluorescein | FDA approved dye |
| 3,5-Dibromo-4-hydroxybenzenesulfonic acid, sodium salt | Topical disinfectant |
| Dibromopropamidine | Cosmetic preservative |
| Diflorasone | Topical anti-inflammatory |
| Dihydroxyacetone | Artificial tanning agent |
| Diisobutyl sodium sulfosuccinate | Wetting agent/detergent |
| Dikegulac | Plant growth regulator |
| Dimethisoquin | Topicai anesthetic |
| Diphenicillin sodium | Antibacterial |
| Diphetarsone | Antiamebic |
| Dipyrone | Analgesic, antipyretic |
| Diquat dibromide | Herbicide, defoliant |
| Dodine | Fungicide |
| Domiphen bromide | Topical anti-infective |
| Dulcin | Non-nutritive sweetener |
| Dymixal ® | Topical burn treatment |
| Ecognidine | Topical anesthetic |
| Edetic acid | Antioxidant |
| Edoxudine | Antiviral |
| Ellagic acid | Hemostatic |
| Endothal | Herbicide, defoliant |
| Eosine I bluish | Dye |
| Eosine yellowish | Cosmetic dye |
| Erythrosine | Food dye |
| Esculin | Skin protectant |
| Ethacridine | Antiseptic |
| Ethambutol hydrochloride | Antibacterial (tuberculostatic) |
| Ethamsylate | Hemostatic |
| Ethylidene dicoumarol | Anticoagulant |
| Ethylstibamine | Antiprotozoal |
| Euprocin dihydrochloride | Topical anesthetic |
| Fast green FCF | Food coloring |
| Fenticonazole nitrate | Topical antifungal |
| Ferric albuminate | Hematinic |
| Ferric chloride hexahydrate | Astringent, styptic |
| Ferric formate | Silage preservative |
| Ferrulic acid, sodium salt | Food preservative |
| Fluorescein, disodium salt | Diagnostic aid |
| Fluoridamid | Plant growth retardant |
| Forminitrazol (Trichomonas) | Antiprotozoal |
| Fortimicin(s) | Antibacterial |
| Foscarnet sodium | Antiviral (HIV-1) |
| Fosetyl Al | Systemic fungicide |
| Pungichromin | Topical antifungal |
| Gallic acid | Astringent, styptic |
| Gentian violet | Topical anti-infective |
| Gluconolactone | Cleaner |
| Gossypol | Rubber antioxidant |
| Heparin | Anticoagulant |
| Hexamethylolmelamine | Fireproofing agent |
| Mexamidine | Antiseptic, anti-acne |
| Homatropine (opthtalmic) | Anticholinergic |
| Hydrastinine hydrochloride | Uterine hemostatic |
| Hydrocortisone phosphate, disodium salt | Glucocorticoid |
| Hydroquinine hydrochloride hemihydrate | Depigmentor |
| Hydroxyamphetamine hydrobromide | Andregenic (opthtalmic) |
| Hydroxybutyranilide | Antioxidant |
| 3-Hydroxycamphor | Topical antipruritic |
| 1-(Hydroxymethyl)-5,5-dimethylhydantion | Cosmetic preservative |
| 8-Hydroxyquinoline sulfate | Antiperspirant, deodorant |
| Iodic acid | Astringent |
| Itraconazole | Antifungal |
| Kanamycin(s) | Antibacterial |
| Kermesic acid | Dye |
| Kojic acid | Flavor enhancer |
| Laccaic acid | Crimson dye |
| Lactic acid | Acidulant |
| Litmus | Indicator |
| L-Lysine L-glutamate | Flavor additive |
| Lyxoflavine | Feedstuff, growth-promoter |
| Maclurin | Dye |
| Malachite green | Dye |
| Maltol | Flavor enhancer |
| Maneb | Agricultural fungicide |
| Manganese acetate | Mordant |
| Meralein sodium | Topical anti-infective |

Plus a host of others, including a wide range of inorganic salts.

The list in Table I is by no means exhaustive as it can be readily determined for each type of particle whether it is capable of forming a hydrogen bond or a coordinate covalent bond. All or most of the particles are non-absorbent and are not superabsorbent polymers. By superabsorbent particles it is meant polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has some particles that will not pass through a 60 mesh screen. Another type of superabsorbent particle is IM 5600 (agglomerated fines). Superabsorbent particulate hydrophilic polymers also are described in detail in U.S. Pat. No. 4,102,340. That patent discloses hydrocolloid absorbent materials such as cross-linked polyacrylamides. Solubility of the particle in water and the binder can be easily ascertained, for example in standard chemical reference materials.

The water soluble particles listed in Table 1 have chemical properties that make them suitable for binding to fibers with the binders of the present invention. The listed particles are organic or inorganic compounds that are water soluble, yet have the capacity to hydrogen bond. Water solubility is preferably high. By water soluble, it is meant a solubility which extends for example, from a lower limit of 10 g in 300 ml of water at 25° C., to an upper limit in which the particle is miscible in all proportions in water at 25° C. This high solubility allows the particles to dissolve when exposed to aqueous liquids such as urine, but the hydrogen bonding capacity allows them to adhere to the fibers in the presence of binder but in the absence of significant aqueous liquid during use by an end user after the manufacturing process is completed. While bound, the particles substantially retain a discrete particulate form instead of dissolving or fusing, at least until they are exposed to an aqueous liquid. More of the particles are discrete rather than agglomerated while bound in the absence of an aqueous liquid.

The amount of particles added to the fibers can vary widely, for example, from 0.05 to 80 percent of the total weight of the fibrous material and particles. Antimicrobials such as chlorhexidine acetate or gluconate are effective in very low amounts, such as 0.05 percent. Modifiers of pH or chelating agents (e.g., sodium bicarbonate or EDTA) are preferably added in an amount of 3–40 percent, especially 15–25 percent by weight of the fibers and particles.

Polymeric Binder Characteristics

The particles may be bound to the fibers by a polymeric binder, which may be water soluble. The polymeric binder comprises binder molecules. The polymeric binder is selected from a predetermined group of polymeric binders wherein the binder molecules each have at least one hydrogen bonding functionality and at least one other hydrogen bonding functionality or a coordinate covalent bond forming functionality on the polymer. In accordance with the present invention, the predetermined groups of polymeric binders include the group consisting of polyglycols [especially poly (propyleneglycol) or polyglycerol], a polycarboxylic acid, a poly(lactone) polyol, such as diols, a polyamide, a polyamine, a polysulfonic acid, and combinations thereof. Specific examples of some of these compounds, without limitation, are as follows: polyglycols may include polypropylene glycol (PPG), polyethylene glycol (PEG), and polyglycerol; poly(lactone) polyols include poly(caprolactone) diol; polycarboxylic acids include polyacrylic acid (PAA); polyamides include polyacrylamide or polypeptides; polyamines include polyethylenimine and polyvinylpyridine; polysulfonic acids or polysulfonates include poly (sodium-4-styrenesulfonate) or poly(2-acrylamido-methyl-1-propanesulfonic acid; and copolymers thereof (for example a polypropylene glycol/polyethylene glycol copolymer). The polymeric binder typically has repeating units. The repeating unit may be the backbone of a compound, such as with a polypeptide, wherein the repeating polyamides occur in the peptide chain. The repeating unit may also refer to units other than backbones, for instance repeating acrylic acid units. In such a case, the repeating units may be the same or different. The polymer has a functional group capable of forming a hydrogen bond or a coordinate covalent bond with water soluble particles, and a hydrogen bond with the fibers.

As used herein, a polymer is a macromolecule formed by chemical union of 5 or more identical or different combining units (monomers). A polyamine is a polymer that contains amine functional groups and a polyamide is a polymer that contains amide functional groups. Each of the binders has at least one hydrogen bonding functionality and at least one hydrogen bonding or a coordinate covalent bonding functionality on the polymer. This functionality may be a hydroxyl, a carboxyl, a carboxylate, a sulfonic acid, a sulfonate, an amide, an ether, an amine or combinations thereof. These binders are capable of forming hydrogen bonds because they have a functional group that contains an electronegative element, such as oxygen or a nitrogen.

The polyglycol has repeating ether units with hydroxyl groups at the terminal ends of the molecule. The polycarboxylic acid, such as polyacrylic acid, has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an electronegative atom, particularly oxygen or nitrogen, on the water soluble particle or fiber to form a hydrogen bond that adheres the binder to the water soluble particle and fiber. The electronegative oxygen or nitrogen of the binder also can form a hydrogen bond with hydrogen atoms in the water soluble particle or fiber that have positive dipoles induced by electronegative atoms, such as oxygens or nitrogens, to which the hydrogen is attached. The polyamide also has a carbonyl group with an electronegative oxygen that can interact with hydrogen atoms in the water soluble particles or fibers. Thus, the polymeric binders can enhance the hydrogen bonding (a) between the fibers and binder; and (b) in the case of water soluble particles with hydrogen bonding functionalities, between the binder and the water soluble particles.

Alternatively, the polymeric binder may form a coordinate covalent bond with the water soluble particles and a hydrogen bond to the fibers. For example, the oxygen or nitrogen on the binder has an unbound pair of electrons that can be donated to an empty orbital in the water soluble particle to form a coordinate covalent bond. For example, one free pair of electrons on the oxygen or nitrogen can be donated to the empty p orbital of a boron-containing water soluble particle to form a coordinate covalent bond that adheres the water soluble particle to the binder. The fibers themselves contain functional groups that can form hydrogen bonds with the binder, and allow the binder to adhere to the fiber. Cellulosic and synthetic fibers may have, for example, hydroxyl, carboxyl, carbonyl, amine, amide, ether and ester groups that will hydrogen bond with the hydroxyl, carboxylic acid, amide or amino groups of the binder. Hence, the polymeric binder will adhere the water soluble particle with a coordinate covalent bond and the fiber will adhere with a hydrogen bond.

In some preferred embodiments, the polymeric binder is bound to both the fibers and the water soluble particle by hydrogen bonds. A polypropylene glycol (PPG) binder, for example, can be used to bind a water soluble particle to cellulosic fibers. The hydroxyl and ether groups on the glycol binder participate in hydrogen bonding interactions with the hydroxyl groups on the cellulose fibers and appropriate functionalities on the water soluble particle, as shown below:

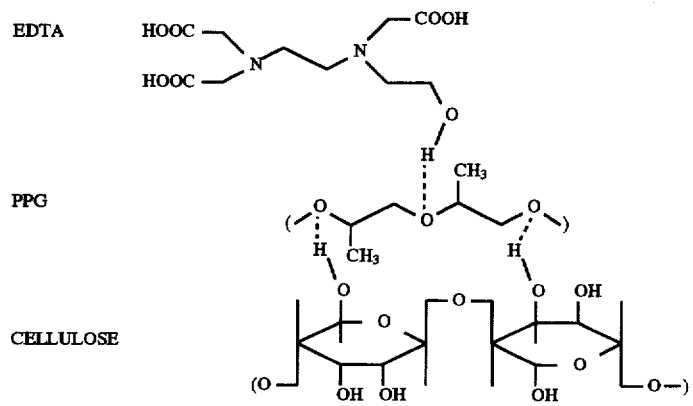

Hence, the binder will adhere both the water soluble particle and fiber with hydrogen bonds. In some embodiments, water may act as a bridge between the fiber and binder, the binder and the particle, or both. Hydrogen bonding interactions with the repeating ether functionality on the glycol binder are shown in the example diagrammed above. A repeating carboxyl group is the bonding functionality on polyacrylic acid, while repeating carbonyls and NR groups (wherein R is either an H or alkyl, preferably lower alkyl i.e., less than five carbon atoms, in a normal or iso configuration) of the amide linkages are some of the bonding functionalities on polyamides such as polypeptides. A repeating amine group is present on polyamines.

The polymeric organic binders of the present invention have been found to improve in binding efficiency as the length of the polymer increases, at least within the ranges of molecular weights that are reported in the examples below. This increase in binding efficiency is attributable to the increasing molecular length. Each of the polymeric binders has a hydrogen bonding or coordinate covalent bonding functionality on the polymer, and longer polymers provide more can allow more flexibility in bridging the fiber to particle gap.

Although the invention is not limited to polymeric binders of particular molecular weights, polymeric binders having a molecular weight greater than 500 grams/mole are preferred because they provide attractive physical properties, the solid is less volatile and less likely to be absorbed by the fiber or the particle, as compared to low-molecular-weight polymeric binders. Polymeric binders with molecular weights greater than 4000 grams/mole are especially preferred because they have minimal volatility and are less likely to evaporate from the fibers or particles. Low-molecular weight materials typically are more mobile than are the higher-molecular weight materials. Low-molecular weight materials can more easily move to the fiber-particle interface, and, over time, are more easily absorbed by the fiber where they are less available to bond the water soluble particles to the fibers. The higher molecular weight materials are less apt to be absorbed by the fibers or the particles, and are less volatile than the low-molecular weight materials. As a result, higher molecular weight polymeric binders, to a greater extent, remain on the surface of the fibers where they are more available to bond water soluble particles to fibers. In some particular embodiments, polymers with molecular weights between 4000 and 8000 grams/mole have been used. Polymers with molecular weights above 8000 may be used, but such exceedingly high molecular weight polymers may decrease binding efficiency because of processing difficulties.

Certain polymeric binders have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Hence, polymeric binders may be preferred that have repeating amine or ether functionalities, more preferably repeating hydroxyl functionalities, and even more preferably repeating carbonyl or carboxyl functionalities, and most preferably repeating amide functionalities. Binding may occur at any pH, but is suitably performed at a neutral pH of 5–8, preferably 6–8, to diminish acid hydrolysis of the resulting fibrous product. Suitable binders may be selected from the group consisting of polyglycols such as polyethylene glycol or polypropylene glycol, polycarboxylic acids such as polyacrylic acid, polyamides, polyamines, and poly(lactone)diols, such as poly(caprolactone) diol.

The group consisting of polycarboxylic acids (such as acrylic acid), polyamides and polyamines has been found to have a especially good binding efficiency. Among polyamides, polypeptides are especially preferred.

Non-Polymeric Binder Characteristics

The water soluble particles may be bound to the fibers by a non-polymeric organic binder. The non-polymeric binders comprise binder molecules. The non-polymeric binder is selected from a predetermined group of binders that each have a volatility less than water. The vapor pressure of the binder may, for example, be less than 10 mm Hg at 25° C., and more preferably less than 1 mm Hg at 25° C. The non-polymeric binder molecules have at least one functional group that is capable of forming hydrogen bonds or coordinate covalent bonds with the water soluble particles. In accordance with the present invention, the predetermined group of non-polymeric binders may include a functional group selected from the group consisting of a carboxyl, a carboxylate, carbonyl, a hydroxyl, a sulfonic acid, a sulfonate, a phosphate, a phosphoric acid, a hydroxy acid, an amide, an amine, and mixtures or combinations thereof (such as an amino acid), wherein each binder includes at least two such functionalities, and the two functionalities are the same or different. A requirement for the non-polymeric binder is that it have a plurality of functional groups capable of hydrogen bonding, or at least one group that can hydrogen bond and at least one group that can form coordinate covalent bonds. As used herein, the term "non-polymeric" refers to a monomer, dimer, trimer, tetramer, and oligomers, although some particular non-polymeric binders are monomeric and dimeric, preferably monomeric.

Particularly preferred non-polymeric organic binders can form five or six membered rings with a functional group on the surface of the water soluble particles. An example of such a binder is an amine or amino acid (for example, a primary amine or an amino acid such as glycine) which forms six membered rings by forming hydrogen bonds.

A six membered ring is also formed by the hydroxyl groups of carboxylic acids, alcohols, and amino acids, for example:

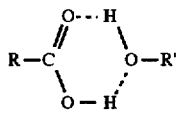

A five membered ring can be formed by the binder and the functionality on the surface of the particle, for example:

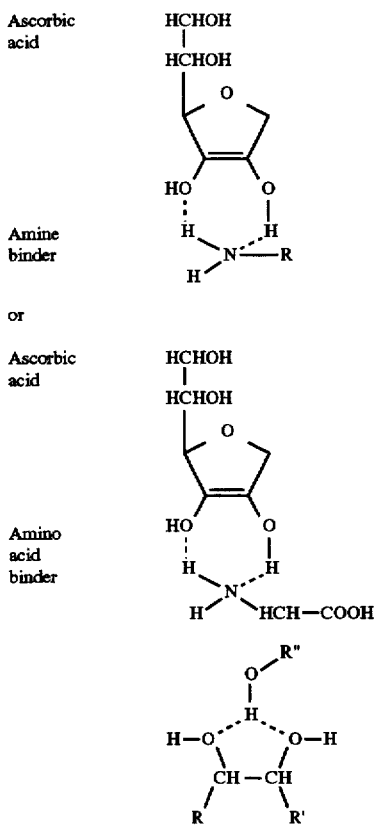

wherein the particle is EDTA and the binder is an alcohol, such as a polyol with hydroxyl groups on adjacent carbons, for example 2,3-butanediol.

Other alcohols that do not form a five membered ring can also be used, for example alcohols that do not have hydroxyl groups on adjacent carbons. Examples of suitable alcohols include primary, secondary or tertiary alcohols.

Amino alcohol binders are alcohols that contain an amine group (—NR$_2$), and include binders such as ethanolamine (2-aminoethanol), diglycolamine (2-(2-aminoethoxy) ethanol)). Non-polymeric polycarboxylic acids contain more than one carboxylic acid functional group, and include such binders as citric acid, propane tricarboxylic acid, maleic acid, butanetetracarboxylic acid, cyclopentanetetra-carboxylic acid, benzene tetracarboxylic acid and tartaric acid. A polyol is an alcohol that contains a plurality of hydroxyl groups, and includes diols such as the glycols (dihydric alcohols) ethylene glycol, propylene glycol and trimethylene glycol; triols such as glycerin (1,2,3-propanetriol); esters of hydroxyl-containing binders also may be used, with mono- and diesters of glycerin, such as monoglycerides and diglycerides, being especially preferred; and polyhydroxy or polycarboxylic acid compounds such as tartaric acid or ascorbic acid (vitamin C):

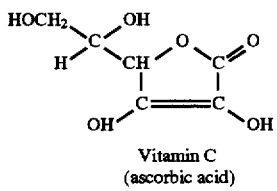

Vitamin C
(ascorbic acid)

Hydroxy acid binders are acids that contain a hydroxyl group, and include hydroxyacetic acid (CH$_2$OHCOOH) and lactic, tartaric, ascorbic, citric, and salicylic acid. Amino acid binders include any amino acid, such as glycine, alanine, valine, serine, threonine, cysteine, glutamic acid, lysine, or β alanine.

Sulfonic acid binders and sulfonates are compounds that contain a sulfonic acid group (—SO$_3$H) or a sulfonate (—SO$_3$). Amino-sulfonic acids also can be used. One example of an amino-sulfonic acid binder suitable for the present invention is taurine, which is 2-aminoethanesulfonic acid.

Non-polymeric polyamide binders are small molecules (for example, monomers or dimers) that have more than one amide group, such as oxamide, urea and biuret. Similarly, a non-polymeric polyamine binder is a non-polymeric molecule that has more than one amine group, such as ethylene diamine, EDTA or the amino acids asparagine and glutamine.

Although other non-polymeric organic binders are suitable in accordance with the discussion above, the non-polymeric organic binder is preferably selected from the group consisting of glycerin, a glycerin monoester, a glycerin diester, a polyglycerol oligomer, propylene glycol, a polypropylene glycol oligomer, glyoxal, ascorbic acid, urea, glycine, pentaerythritol, a monosaccharide, a disaccharide, citric acid, taurine, tartaric acid, dipropyleneglycol, urea derivatives, and combinations thereof. The non-polymeric binder also is most preferablyselected from the group consisting of glycerin, a glycerin monoester, a glycerin diester, a polyglycerol oligomer, propylene glycol, urea and combinations thereof. The non-polymeric binders also preferably include functionalities selected from the group consisting of a carboxyl, a carboxylate, a carbonyl, a sulfonic acid, a sulfonate, a hydroxy acid, a phosphate, a phosphoric acid, a hydroxyl, an amine, an amide, and combinations thereof. The non-polymeric binders may have at least two functionalities from such group, and the groups may be the same or different.

Each of the non-polymeric binders disclosed above is capable of forming hydrogen bonds because it has a functional group that contains an oxygen or nitrogen, or has oxygen or nitrogen containing groups that include a hydrogen. The amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an NR group in which a hydrogen may be bound to an electronegative nitrogen that also leaves the hydrogen partially positively charged. The partially positively charged hydrogen in both cases then can interact with an oxygen or nitrogen on the particle or fiber that adheres the binder to the particle and fiber. The polycarboxylic acid, hydroxy acid, amino acid and amide also have a carboxyl group with an electronegative oxygen that can interact with hydrogen atoms in the particles and fibers. Similarly, electronegative atoms (such as oxygen or nitrogen) on the fiber or particle can interact with hydrogen atoms on the binder that have positive dipoles, and partially positive hydrogen atoms on the fiber or particle can interact with electronegative atoms on the binder.

Several proposed hydrogen bonding interactions of two of the binders (glycine and 1,3-propanediol) with cellulose are shown below:

empty orbital of an acceptor atom in the water soluble particle to form a coordinate covalent bond. The free pair of electrons on the oxygen or nitrogen can be donated to the empty p, d or f orbital of a water soluble particle (for example a boron containing particle) to form a coordinate covalent bond that adheres the particle to the binder. The fibers themselves do not normally contain functional groups that can form coordinate covalent bonds with the binders, but hydrogen bonding interactions allow the binder to adhere to the fiber. Cellulosic and synthetic fibers, for example, contain hydroxyl, carboxyl and ester groups that will hydrogen bond with the hydroxyl, carboxylic acid, amide, amine, or other groups of the binder. Non-cellulosic or non-synthetic fibers that have these functionalities can also be used, for example silk, which has an amide linkage. Hence the binder will adhere the particle with a coordinate covalent bond and the fiber with a hydrogen bond.

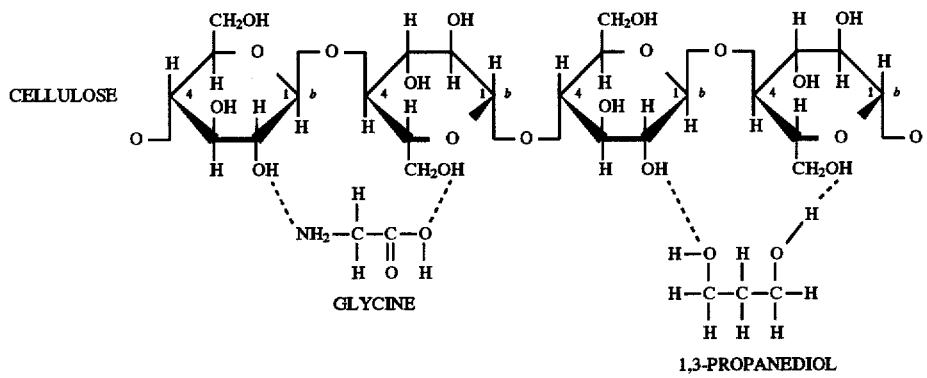

The hydrogen bonding interactions are shown as dotted lines. One such interaction is shown between the nitrogen of glycine and a hydrogen of an OH on cellulose. A hydrogen bond with glycine is also shown between an oxygen of the OH on glycine and the hydroxy hydrogen of an alcohol sidechain on cellulose. Hydrogen bonding interactions of the 1,3-propanediol are shown in dotted lines between an oxygen on an OH group of the binder and a hydrogen of an OH group on the cellulose molecule. Another hydrogen bond is also shown between a hydrogen on an OH group of the glycol binder and an oxygen in an alcohol sidechain of the cellulose.

It also is possible for water or other hydrogen bonding molecules to be interposed between the fiber and binder, such that the fiber and binder are both hydrogen bonded to the water molecule.

Alternatively, an atom on the binder may have an unbound pair of electrons, such as a lone pair of electrons from an oxygen or nitrogen atom, that can be donated to an In some preferred embodiments, the binder is bound to both the fibers and the water soluble particle by hydrogen bonds. A polyol binder, for example, can be used to bind EDTA particles to cellulosic fibers. The hydroxyl groups on the polyol binder participate in hydrogen bonding interactions with the hydroxyl groups on the cellulose fibers and the carboxyl groups on the EDTA. Hence the binder will adhere to both the particle and fiber with hydrogen bonds. These hydrogen bonds provide excellent binding efficiency and diminish separation of bound particles from the fibers.

A structural drawing is shown below in which citric acid, vitamin C and urea adhere water soluble EDTA particles to cellulose with hydrogen bonds. Some of the possible hydrogen bonding interactions are shown as dashed lines. It is possible that other molecules (such as water molecules) also may participate in some of these bonds, for example, as an intermediary between the binder and particle or fiber.

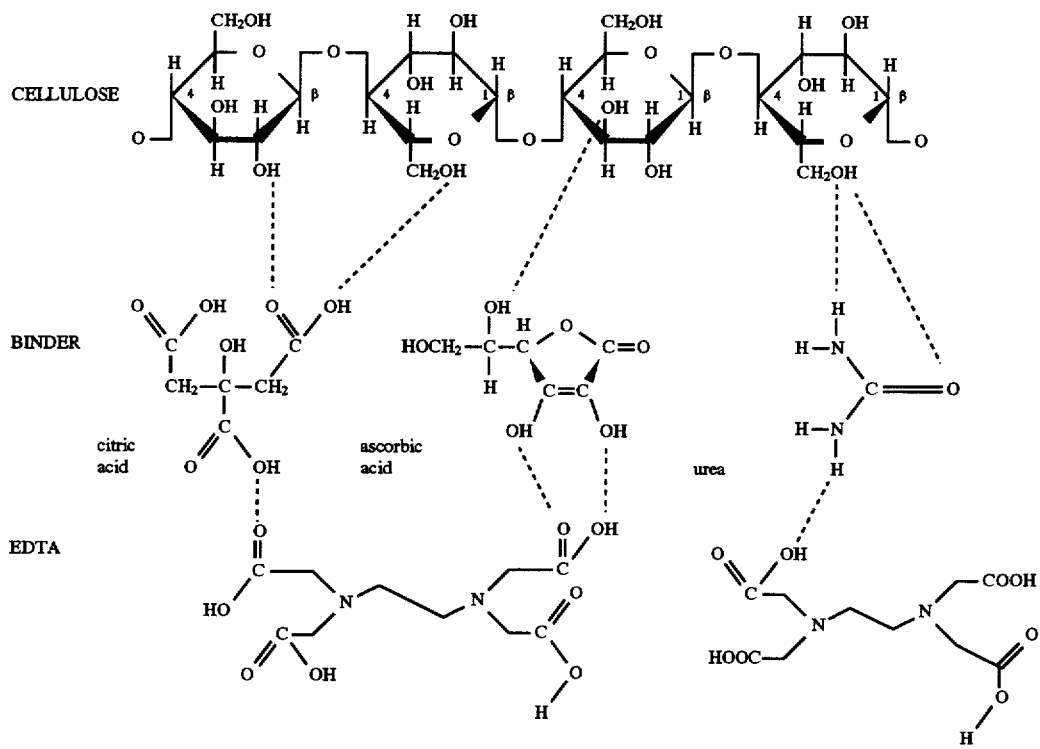

Particularly efficient hydrogen bonding binders include those with carboxyl groups, such as ascorbic acid, or amide groups, such as urea. Hydroxyl groups are also very efficient binders. Amine and ether functionalities are less efficient binders.

Binders have functional groups that may be selected independently or in combination from the group consisting of a carboxyl, a carboxylate, a carbonyl, a hydroxyl, a sulfonic acid, a sulfonate, a phosphoric acid, a phosphate, a hydroxy acid, an alcohol, an amide and an amine, and combinations or mixtures thereof. The binder molecule has at least two of these functional groups, and each of the functional groups can be the same (for example, a polyol, polycarboxylic acid, glyoxal, and polyamine or polyamide) or different (for example, an amino alcohol, hydroxyamide, carboxyamide, or amino acid). Functional groups may also be selected independently or in combination from the group consisting of a carboxylic acid alone; a carboxylic acid and an alcohol; a carboxylic acid, a hydroxy acid, an amino acid, and a carboxyamide; a carboxylic acid, an alcohol and an amide; an amino acid, an amide, and an amine; a polyol and an amino alcohol; a carboxylic acid, an alcohol, an amide and an amine; an alcohol alone; an alcohol and an amide; an alcohol, an amide and an amine; an amide alone; an amide and an amine; and an amine alone. An aldehyde may optionally be a member of any of these groups, particularly if it is oxidized to a carboxylic acid.

These functional groups might be provided by the following exemplary chemical compounds: a carboxyl group could be provided by carboxylic acids, such as ascorbic acid; a carboxylate, which is an ionized carboxylic acid, could be provided by a material such as calcium ascorbate; a carbonyl group can be provided by an aldehyde, or ketone, a hydroxyl, such as an alcohol or polyol, could be provided by a material such as glycerol, or a mono- or diglyceride, which are esters of glycerol; an amide, such as a peptide; and an amine, which may be provided by an alkyl amine, such as ethanolamine.

Without limiting these combinations of functional groups, preferred functional groups for the non-polymeric binders may be selected independently or in combination from the group consisting of an amino alcohol, a polycarboxylic acid, a polyol, a hydroxy acid, an amino acid, an amide, and a polyamine. Other preferred groups of binders include an amino alcohol alone, an amino alcohol and a polycarboxylic acid, an amino alcohol, a polycarboxylic acid and a polyol; an amino alcohol, a polycarboxylic acid, a polyol and a hydroxy acid; an amino alcohol, a polycarboxylic acid, a polyol, a hydroxy acid and an amino acid; an amino alcohol, a polycarboxylic acid, a polyol, a hydroxy acid, an amino acid and an amide; a polycarboxylic acid and a polyol; a polycarboxylic acid, a polyol and a hydroxy acid; a polycarboxylic acid, a polyol, a hydroxy acid, and an amino acid; a polycarboxylic acid, a polyol, a hydroxy acid, an amino acid and an amide; a polycarboxylic acid, a polyol, a hydroxy acid, an amino acid, an amide and a polyamine; a hydroxy acid and an amino acid; a hydroxy acid, amino acid and amide; a hydroxy acid, amino acid, amide and polyamine; an amino acid and an amide; an amino acid, amide and a polyamine; an amide and a polyamine; an amino alcohol alone, a polycarboxylic acid alone, a polyol alone, a hydroxy acid alone, an amino acid alone, an amide alone and a polyamine alone.

Again, without limiting the invention and more specifically, the functionalities of the non-polymeric binder may be selected from the group of glycerin (a polyol), ascorbic acid (a polycarboxylic acid and a hydroxy acid), glyoxal (a polyaldehyde), urea (a polyamide), glycine (an amino acid), pentaerythritol (a polyol), a monosaccharide, a disaccharide (a polyhydric alcohol), as well as citric acid, tartaric acid, dipropylene glycol, and urea derivatives such as DMDHEU. Subgroupings include glycerin; glycerin monoesters; glycerin diesters; polyglycerin oligomers; propylene glycol; polypropyleneglycol oligomers; glycerin and ascorbic acid; glycerin, ascorbic acid and urea; glycerin, ascorbic acid, urea and glycine; glycerin, ascorbic acid, urea, glycine and pentaerythritol; taurine; glycine, ascorbic acid, urea, glycine, pentaerythritol and a monosaccharide; glycerin, ascorbic acid, urea, glycine, pentaerythritol, a monosaccharide and a disaccharide; ascorbic acid; ascorbic acid and urea; ascorbic acid, urea and glycine; ascorbic acid, urea, glycine and pentaerythritol; ascorbic acid, urea, glycine, pentaerythritol and a monosaccharide; ascorbic acid, urea, glycine, pentaerythritol, monosaccharide and a disaccharide; urea; urea and glycine; urea, glycine and pentaerythritol; urea, glycine, pentaerythritol and a monosaccharide; urea, glycine, pentaerythritol, a monosaccharide and a disaccharide; glycine; glycine and pentaerythritol; glycine, pentaerythritol and a monosaccharide; glycine, pentaerythritol, a monosaccharide and a disaccharide; pentaerythritol; pentaerythritol and a monosaccharide; pentaerythritol, a monosaccharide and a disaccharide; a monosaccharide; a monosaccharide and a disaccharide; and a disaccharide.

Combinations of polymeric and non-polymeric binders may also be used, providing that they are non-reactive. That is, providing that the binders do not react in a manner which prevents the binders from possessing the functional groups required to be present for binding in accordance with the present invention.

Process Advantages

The binders of the present invention also provide numerous process advantages. Binding of particles to the fibers can occur, for example, without external application of heat. Hence particle binding may occur at ambient temperature if desired. The present invention is therefore distinct from prior art crosslinking processes in which elevated temperatures are required to covalently crosslink cellulose groups to one another. Moreover, the binders of the present invention may be activated or reactivated by the addition of a fluid, such as a liquid solvent (sometimes referred to herein as a reactivation or activation liquid, one example of which is water). Hence, a liquid binder (which would include a solution of a solid or liquid binder, or a binder that has a melting point below room temperature) can be applied to a cellulose mat in the absence of the particles to be bound and the binder allowed to dry, for example until the fiber product reaches an equilibrium moisture content with the moisture in the ambient air. The binders may then be activated to bind the particles in place. Some of the binders (especially the liquid binders) diffuse throughout the fibers to reach an equilibrium distribution of the binder. Alternatively, the binder can be applied as a solid, for example as particles or a powder. At a later stage of processing, water or another activating fluid or liquid may be added to those portions of the mat where particulate binding is desired. The particles then may be added to the mat and adhered to those portions of the mat that have been moistened. Alternatively, the particles may be added to the mat prior to or simultaneously with activation of the binder. Activation of binders is more fully described in U.S. Pat. No. 5,352,480 filed Aug. 17, 1992, which is incorporated by reference.

The binders may be liquids at room temperature (such as glycerin), or liquid solutions of binders that are solids at room temperature (for example, an aqueous solution of glycine), or liquid hot melts of solid binders. Solid binders may be added to fibers in particulate form, for example, by sprinkling binder particles on the fibers provided they are fixed by the subsequent application of heat or liquid.

The binding reaction of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis. A non-acidic pH (7 or greater) will provide an environment that inhibits formation of ester bonds, and promotes formation of the hydrogen bonds or coordinate covalent bonds that adhere the particles of the present invention to the fibers with the binder.

To reduce dissolving of the particles into the binder when water soluble particles are used, the moisture content of the fibers during the water soluble particle binding reaction is 0.5–30%, suitably 5–25%, and preferably 12–20% water by weight of the fibers, binder and particle. Higher moisture content may be present, but if present when the particles are added the particles tend to dissolve to a greater extent. A moisture content greater than 20% can be used even though such high moisture contents would interfere with intermediate anhydride formation and inhibit formation of covalent bonds in the production of some high bulk crosslinked fibers. Particles may be added to the fibers such that the particles are distributed throughout a fibrous product without being confined to a surface of the product. The particles can be distributed throughout the depth of a fiber product such as a mat or web.

The binder is suitably present in the treated product in an amount of at least about 1 percent and no more than 80 percent by weight of the fibers ("percent by weight"). In especially preferred embodiments, the binder is present in an amount of 3–60, or more preferably 5–30 percent by weight. However, when the binder is first placed on the fiber with binder amounts below about 1 percent, an insufficient amount of binder is present to achieve adequate binding. Using excessive amounts of binder can introduce unnecessary expense into the binding process. High percentages of binder can also cause processing problems because the binder material transfers to equipment surfaces. The presence of excessive binder may also dissolve the water soluble particles. Therefore it is often preferred to use no more binder than is required to bind the particles and fibers.

Thermoplastic binders may also be used to help bind fibers to each other and particles to fibers, as long as the particles are not themselves soluble in the thermoplastic binder. The binder that has the hydrogen bonding or coordinate covalent bonding functionalities may itself be thermoplastic. Some polymeric and some non-polymeric binders of the present invention have the advantage of being meltable solids. Hence fibers treated in accordance with the present invention can be thermobonded by elevating the fiber temperature above the melting temperature of the binder to melt the binder and physically bind the fibers to each other and the fibers to the particles. Alternatively, an auxiliary or second binder can be applied to the fibers as a solid at room temperature, and the temperature of the second binder elevated above its melting point to thermobond the fibers and particles. The auxiliary binder may be applied to the fibers either before or after the primary binder is applied, but before thermobonding.

The binders of the present invention may be used with fibers that have substantial intrafiber covalent crosslinks (such as HBA files available from Weyerhaeuser) or fibers which are substantially free of intrafiber covalent crosslinking. Examples of individualized intrafiber crosslinked fibers are seen in European Patent Applications 440 472 A1 and 427 317 A2, which produce products that those publications describe as being substantially free of interfiber bonds. Those fibers have been individualized and then cured in the presence of a crosslinking material at an elevated temperature to produce high bulk fibers having intrafiber covalent crosslinks. The fibers of the present invention do not need to be processed as in those European applications to eliminate interfiber bonds. Binders of the present invention can therefore be used with natural fibers that have substantial interfiber bonding, which is defined as fibers that have not been processed as in European Applications 440 472 A1 and 427 317 A2 to substantially eliminate interfiber bonds. Cellulose fibers that have not been so processed are substantially free of intrafiber bonds.

Although intrafiber covalent crosslinking is not required for the present invention, such high bulk fibers can be used with the binders disclosed herein. Fibers that have high bulk from intrafiber covalent crosslinks are prepared by individualizing the fibers and curing them at an elevated temperature (above 150° C.) in the presence of a crosslinking material such as 1,2,3,4-butane tetracarboxylic acid. Initial application of the binder selected in accordance with the present invention on such high bulk fibers may occur after the curing step, particularly if the binder is capable of functioning as a crosslinking material. The binders disclosed herein that can also crosslink are polyols, polycarboxylic acids, and polyamines (both polymeric and non-polymeric binders that have more than one amine group); none of the other specifically disclosed binders are known to form covalent, intrafiber bonds. If crosslinking binders are present during curing, the binder can be consumed during the curing step to form covalently crosslinked bonds. When this occurs, the binder's functionality is no longer available for hydrogen bonding, and particle binding to fibers is ineffective without another binder of this invention to provide the desired functionalities.

However, the binder can be applied before curing, even if the binder is also a crosslinking material, if steps are taken to retard covalent bond formation. Covalent bond formation can be inhibited, for example, by adding a sufficient amount of water to the fibers to prevent condensation reactions from occurring until the water has evaporated, thereby limiting the time available for crosslink bond formation. Prevention of condensation reactions can occur when the fibers have 20% water by weight of the fiber and are cured at 150° C. for 20 minutes. Hence, at least 20% water (preferably 30%) by weight of the fiber should be present, or 20–50% water. Higher amounts of water within this range are preferred when curing at temperatures higher than 150° C., or for periods of time longer than 20 minutes. However, at the time the water soluble particles are added, it is preferable that the water content is reduced to no more than 30%, or lower, to reduce the extent of particles being dissolved as they are being bound in place.

In accordance with this invention, the binders may be applied to fibers before, subsequent to, or simultaneously with addition of the particles. Simultaneous addition can be accomplished by two separate streams of particles and binder that are simultaneously directed at a fibrous substrate, or alternatively merged immediately prior to impacting against the substrate. The binder also may be applied first to the particles, with the subsequent mixing of the particles with fibers. Without limiting the invention, it appears that the addition of some small amounts of moisture to the particles may help bind the particles to the fibers. The addition of water may occur before, subsequent to or simultaneously with the addition of fiber.

The fibrous product of the present invention (with or without intrafiber crosslinking) may further be densified by external application of pressure. The densified product is compact and easily transported. And, if superabsorbent particles are also included in the product, the resulting fibrous product has superior absorbent properties as compared to nondensified products. The inventors have found that the binders of the present invention produce a product that can be easily densified. Easy densification is associated with the hydrogen bonds and coordinate covalent bonds formed between the binder and the particles and fibers. The fibers are particularly easily densified when at least 5% by weight of the fibers, particles and binder, more preferably 10%, are particles adhered to the fibers.

Binding may be performed under conditions that favor formation of hydrogen bonds or coordinate covalent bonds, and discourage formation of covalent bonds. Conditions that favor covalent bonds are those disclosed in U.S. Pat. No. 4,412,036 and U.S. Pat. No. 4,467,012 wherein particle and binder would be laminated between tissue layers under high temperature and pressure to form laminated adherent tissue layers. That patent teaches that minimal adhesion occurs at 200 pli (pounds per linear inch, as in a calender press) if no external heat is supplied, but adhesion improves as the reaction temperature increases. Improved adhesion of the tissue layers occurs because of enhanced covalent bonding as the temperature increases.

Conditions that favor covalent bond formation are also shown in European Patent Applications 440 472 A1; 427 317 A2; 427 316 A2; and 429 112 A2. These European publications use polycarboxylic acid crosslinkers, and require elevated temperatures (for example above 145° C.) and acidic conditions (pH less than 7) to promote formation of intrafiber covalent ester bonds and inhibit reversion of the ester bonds. The present invention, in contrast, can form hydrogen or coordinate covalent bonds below 145° C., below 100° C., and even at room temperature. The binders of the present invention can also bind particles to fibers under neutral or alkaline conditions, i.e., at a pH above 7, but preferably at a pH of 5–8 or 7–8.

The intrafiber covalent bond forming processes described in the above European publications require formation of an anhydride that then reacts with a hydroxy group on cellulose to form a covalent ester bond. The presence of more than about 20% water by weight in the fibers is believed to delay the formation of intermediates and inhibit covalent bond formation. Hence, in processes that use binders that are also crosslinkers (polycarboxylic acid, polyols and polyamines) as binders in the present invention, the fibers should contain at least 20% water by weight (more preferably 30%) if the water soluble particles and binder are present in the fibers when curing occurs. The water serves to shorten cure time, thereby inhibiting covalent bond formation, thus preventing all of the binder from being used to form covalent intrafiber crosslinks. Hence, some of the binder remains available to form the non-covalent bonds with the water soluble particles and produce ease of densification in fiber products made by the process of the present invention.

The present invention, in contrast, produces a product under conditions that favor formation of hydrogen or coordinate covalent bonds. Hence, the particles can be bound to the fibers in the absence of the external application of heat or pressure. Particles may also be bound and the resulting fiber product densified, for example at less than 200 pli (about 8000 psi), or less than 100 pli (about 4000 psi) with SAP, in the absence of external application of heat to produce a product in which a substantial portion of the water soluble particles are bound by non-covalent bonds (hydrogen or coordinate covalent bonds). A substantial portion of water soluble particles bound by non-covalent bonds means at least half of the particles are bound by other than covalent bonds, for example by hydrogen or coordinate covalent bonds.

In yet other examples, particles may be bound in the absence of external application of pressure, but at elevated temperatures.

In particularly preferred embodiments, the particles are substantially entirely bound to the fibers non-covalently.

Binding Examples

Several examples are given below illustrating use of the binders of the present invention to attach particles to southern bleached kraft pulp.

EXAMPLE I

A 321 gram amount of NB-416 southern bleached kraft fluff obtained from Weyerhaeuser Company (Tacoma, Wash.) was air-entrained in a blender-like mixing device and 50 grams of glycerin (supplied by Dow Chemicals of Midland, Mich.) was sprayed onto the fluff. Then 288 grams of disodium ethylenediamine tetraacetic acid (EDTA) (supplied by Mallinkrodt Chemical Works of St. Louis, Mo.) was added and mixed in the device. The blender was stopped, the product was vacuumed out, and spread out in a fume hood to dry overnight. The resulting product was examined by scanning electron microscope (SEM) and revealed disodium EDTA particles attached to fibers.

Glycerin is advantageous because it tends to penetrate the fibers and soften them in addition to binding the water soluble particles to the fibers. However, over time less glycerin is available at the surface of the fibers for use in binding water soluble particles in the event the glycerin/fiber material is stored for long periods prior to use in adhering water soluble particles (e.g. if activation is delayed for several weeks or more). This can be compensated for in part by using higher percentages of glycerin on the fibers. Also, monoglyceride and diglyceride binders do not penetrate as readily into the fibers and therefore can be stored longer before activation to adhere water soluble particles. In the glyceral and urea combination the amount of urea used will by effective to prevent the penetration of the glyceral into the fiber.

EXAMPLE II

A 321 gram amount of HBA fiber (a crosslinked high bulk fiber available from Weyerhaeuser Company, Tacoma Wash.) was air-entrained in a blender-like mixing device and 50 grams of glycerin (supplied by Dow Chemical of Midland, Mich.) was sprayed onto the fluff. Then 288 grams of sodium bicarbonate (supplied by J. T. Baker Chemical Co. of Phillipsburg, N.J.) was added and mixed in the device. The blender was stopped, the product was vacuumed out, and spread out in a fume hood to dry overnight. The resulting product was examined by scanning electron microscope and revealed fibers with attached sodium bicarbonate particles.

EXAMPLE III

An NB 416 pulp sheet (southern bleached kraft available from Weyerhaeuser Company of Tacoma, Wash.) was treated with glycerin on a roll coater so that the product contained 10% glycerin by weight. That pulp sheet was fed into a hammermill and ground while simultaneously adding a polyacrylate hydrogel (IM 3900, supplied by Hoechst Celanese of Portsmouth, Va.) and ethylenediamine tetraacetic acid to the mill at rates such that the product contained 54% treated fiber, 42% IM 3900, and 4% EDTA. That mixture was shunted to an airlay device from J&J Machines (of Horsens, Denmark) and airlaid into a continuous web. The resulting product was examined by scanning electron microscope and revealed fibers with attached polyacrylate hydrogel and EDTA particles.

EXAMPLE IV

A procedure similar to the one described in Example III was performed using Kittyhawk pulp (a thermobondable blend of southern bleached kraft and polyethylene fibers available from Weyerhaeuser Company of Tacoma, Wash.). The resulting product was thermobonded by passing the web through a through-air oven at 140° C. for 0.5 minutes. The resulting product was examined by scanning electron microscope, and revealed fibers with attached polyacrylate hydrogel and EDTA particles.

EXAMPLE V

Figure 13:
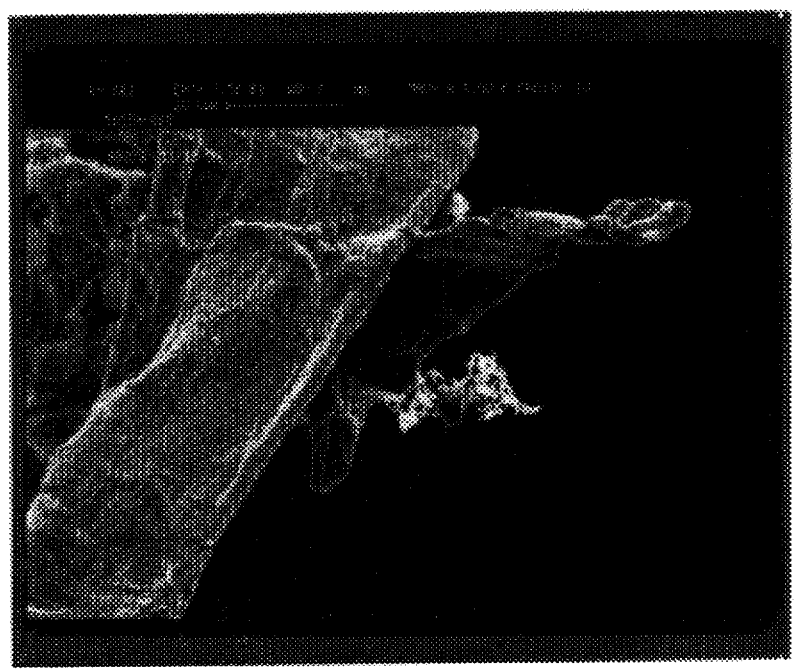
FIG. 13 is a photomicrograph of oxalic acid particles bound to a fiber with a glycerin binder.

In this example, oxalic acid is bound to the fibers by the binders of the present invention. A pulp sheet with 10% binder was prepared as in Example III. The pulp sheet was conditioned at 90% relative humidity for 4 hours, then the sheet was fiberized in a Waring blender. Particles of oxalic acid were then added to the blender and blending continued. The product was dried and an SEM obtained, which is shown in FIG. 13. The feathery particle of oxalic acid is shown near the center of the photograph bound to the cellulose fiber by the glycerin.

EXAMPLE VI

Figure 14:
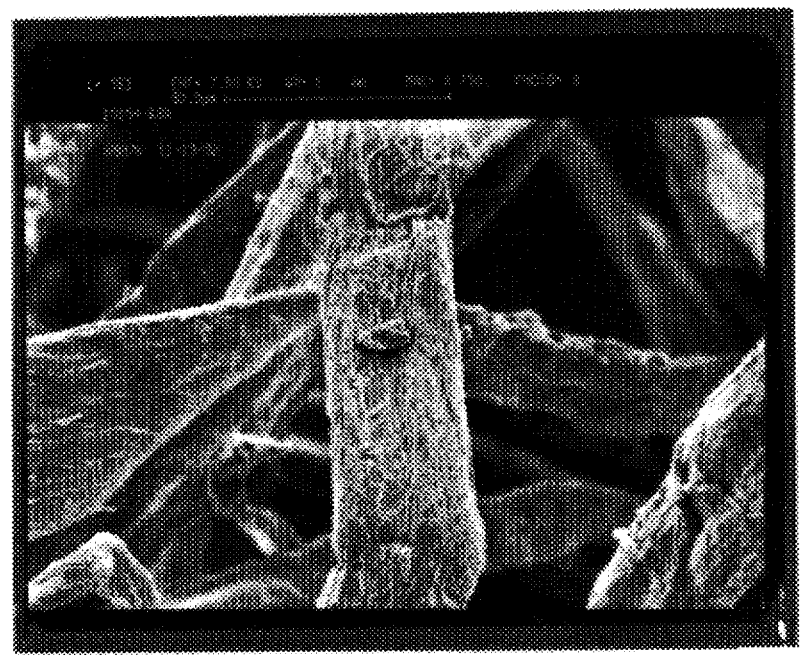
FIG. 14 is a photomicrograph of aluminum sulfate (alum) bound to a fiber with a glycerin binder.

Fibers were prepared as in Example V, except aluminum sulfate (alum) was substituted for oxalic acid. The SEM of alum bound to the fibers is shown in FIG. 14.

EXAMPLE VII

A mixture of binders may also be used to bind particles to the fibers. Fibers may be supplied as in Example I, but the 50 grams of glycerin would be substituted with a mixture of urea and glycerin. A 40/60 mixture (by weight) of urea and glycerin is mixed by dissolving urea in the glycerin, and heating the solution to 70°–80° C. The heated binder mixture is then applied to bind the particles to the fibers as in Example I. The urea/glycerin mixture provides several advantages over the use of glycerin alone. Urea lowers the cost of the binder, while glycerin softens the fibers. The mixture also provides manufacturing advantages.

In other embodiments urea alone as well as the other binders of the type specified in the foregoing detailed description of the invention and combinations thereof may be used as the binder. Also, auxiliary binders (additional binders) may be used in addition to the binder or binder combinations with a functionality in accordance with the present invention providing that the additional binder(s) does not react with the binder or binder combination of the invention to prevent this latter binder or binder combination from having the required functuality.

EXAMPLE VIII

Activation

The binders of the present invention have the advantage of being activatable by addition of liquid in which the particle is sparingly soluble or insoluble, by heating, or by kinetic energy such as is supplied by mechanical agitation. As stated above, "activation" includes activating a previously inactive binder (e.g., by adding liquid to a solid) or reactivating a previously active binder (e.g., by adding liquid to a dried liquid binder) on the fibers. Hence, a liquid binder can be applied to cellulose fibers, loose or in another form, such as a cellulose mat, in the absence of the particles to be bound. The binder is then dried or allowed to dry, for example until the binder and fiber reach an equilibrium moisture content with ambient air. Alternatively, the binder can be applied as a solid, for example, particles sprinkled onto a fiber mat. At a later stage of processing, a liquid such as ethanol (EtOH) is added to the fibers resulting in an activation of the binder. The water soluble particulates may then be added, and the binder secures the particulates to the fibers. This subsequent processing of the fibers to attach the water soluble particles can occur, for example, at a separate location from the location where the binder was applied to the fibers. Therefore, manufacturers of products can add particulates of interest (e.g., hemostatics, antimicrobial particles, etc.) at the place of manufacture of the end products that incorporate the treated fibers. Also, more than one type of particulate material (e.g. both water soluble and non-water soluble particles with the required functionality or particles without this functionality) may be added, if desired. It has also been found that some of the binders of the present invention can be activated by the application of kinetic energy such as by mechanical agitation. For example, glycerin binder may be applied to fibrous cellulose. The glycerin binder may be allowed to dry. The fibers then may be mechanically agitated in the presence of water soluble particles, with or without superabsorbent particles, to activate the glycerin binder and bind the particles to the fibers. Mechanical agitation may take place, for example, in a defiberizer where a sheet or mat of glycerin treated cellulose fibers are defiberized while being intimately mixed with particles that become bound to the fibers by the mechanical agitation.

Binder Activation Examples

Binder activation in the present invention allows binder to be added to fibers either before or after the water soluble particles are added to the fibers. The binder is subsequently activated by addition of liquid, heat, or by kinetic energy such as resulting from agitation, and the water soluble particles become bound to the fibers. The activation liquid is most preferably selected such that the water soluble particles are insoluble in the liquid. Otherwise the particles would dissolve to a significant extent during activation, depending upon the quantity of activation liquid which is used. The water soluble particles may be added to the fibers either before binder activation, after binder activation, or simultaneous with activation. If the water soluble particles are to be added to cellulose fibers, for example, the binder (e.g. glycerin) may be applied to a pulp sheet which is subsequently fiberized. A liquid such as EtOH or acetone may be added to the pulp before or after fiberization, and the water soluble particles may be added before or after liquid addition, or simultaneously with the liquid. If the water soluble particles are added after liquid addition, the particles should be applied to the fibers prior to complete evaporation of the added liquid from the fibers. The liquid can be added in any way, such as by fogging, misting or spraying the liquid.

Activation can be of all the fibers, or only portions of the fibers, such as target zones or portions of the mat where particulate binding is desired. The particles may then be added to the mat and adhered to the target zones of the mat which have been activated. In some embodiments, the binder is applied as a solid and heated during a later processing stage to activate the binder by softening it such that it binds the particles to the fibers. The particles may be added in a pattern corresponding to a desired (for example, a non-homogeneous distribution) distribution of particles in the fibrous material. Most commonly, however, activation is accomplished by using an activating fluid to moisten a targeted area of the product into which an inactive (dry or dried) binder has already been introduced. In yet other embodiments, the binder is applied to the fibers and then activated by applying kinetic energy to the fibers. Neat polypropylene glycol (MW 2000) binder, for example, may be sprayed on fibers and allowed to dry. Desired particles are then added to the fibers as the fibers are mechanically agitated in a blender or defiberizer to kinetically activate the binder and bind the particles to the fibers. For kinetic activation, the binder may be added as a liquid or a solid to the fibers. In the case of liquid addition, the liquid is allowed to dry, and then activated by mechanically agitating the fibers and binder. In the case of solid binder addition, the binder is applied as a solid, and then moistened (for example, to a total fiber moisture content of about 7%) and then mechanically agitated.

Activation of the binder may be performed prior to adding the particles, subsequent to adding the particles, or simultaneously with addition of the particles. Once the binder is activated, it adheres a substantial portion of the particles to the fibers, wherein "a substantial portion" refers to at least about half of the particles present in the fibers, at least where the particles are not added in excess. More typically substantially all of them, e.g., over 80% are adhered to the fibers.

In embodiments in which the binder is applied to the fibers as a solid, the activating step can comprise applying a liquid to the fibers after the binder has been applied to the fibers, shortly before the binder is applied to the fibers, or simultaneously with application of the binder to the fibers.

The activating step is preferably performed after the curing step is complete, if a curing step is to be performed.

Thermoplastic Binders

An auxiliary binder may also be used to help bind fibers to each other above the melting point of the auxiliary binder. The auxiliary binder may be a solid thermoplastic material that is applied to the fibers and softened by elevating the temperature during the binding step to above the softening temperature of the auxiliary binder. The auxiliary binder is thereby temporarily softened, rendered more fluid (which for purposes of convenience may be referred to as auxiliary binder softening) and subsequently resolidified as the temperature cools, which thermoplastically binds the fibers to each other, and the particles to the fibers. The auxiliary binder may also contain a hydrogen bonding functionality that hydrogen bonds the particles to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such auxiliary binders can be found in U.S. Pat. No. 5,057,166.

The auxiliary or second binder can be added to the fibers, either before or after a first binder, to help bind the fibers to each other and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials: ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acrylic acid, polyethylene, urethanes, polycarbonate, oxide, polypropylene, polyesters, and polyimides. In addition, a few specific examples of thermoset binders include those made of the following materials: epoxy, phenolic, bismaleimide, polyimide, melamine/formaldehyde, polyester, urethanes, urea, and urea/formaldehyde.

More than one of these materials may be used to treat the fibers. For example, a first coating or sheath of a thermoset material may be used followed by a second coating of a thermoplastic material. The water soluble particles that have limited solubility in the binder are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby products made from these fibers. For example, polyvinyl chloride, polyvinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

EXAMPLE IX

As previously described, an auxiliary binder can be used in addition to the polymeric binders of the present invention. A 3210 gram amount of southern bleached kraft binder (NB-416, supplied by Weyerhaeuser Company) is air entrained in a blender-like mixing device and sprayed with 2128 grams of a polyvinyl acetate latex (PN-3666H, supplied by H. B. Fuller of Minneapolis, Minn.). While still mixing, 189 grams of a EDTA is added and the resulting mixture is then sprayed with 580 grams of polypropylene glycol (supplied by Union Carbide of Danbury, Conn.). The blender is then stopped and the mixture then airlaid as a 16 inch wide web on a Danweb airlay machine, pressed to a density of approximately 0.15 g/cc, and thermobonded at 140° C. for thirty seconds. The resulting web would have 4% bound EDTA and improved tensile strength (as compared to untreated fluff with SAP).

Application of Binder

The binders of the present invention can be added to the fibers in any convenient manner. One such procedure is to spray the binder or binders on a web of the fibers that is conveyed past a sprayer on a conveyor belt. Alternatively, loose fibers may be allowed to fall past a sprayer, or loose fibers may be moved on a conveyor belt past a sprayer. The loose fibers may also be slurried with or immersed in binder. For solid binders, blending of the fiber and binder may be accomplished or the binder may simply be sprinkled onto or otherwise comingled with the fibers followed by a fixation step such as heat or addition of liquid. The fibers may also be sprayed or immersed in the binder, or binder particles may be applied thereto. These fibers can, while still wet in the case of a liquid binder or following activation of a liquid or solid, be combined with the water soluble particles. The fibers can also be allowed to dry for later activation with an reactivation fluid, such as an activation liquid, and combined with the water soluble particles at that time. An example of when it may be desirable to apply the binder to the fiber and thereafter activate the binder in the presence of particles is when the particles are added at a remote site. For instance, the binder may be activated from an inactive state at a second location that is remote from a first location where the binder is applied to the fibers. The second location may be, for example, a location where a manufacturer combines fibers and particles into articles, such as absorbent articles. Particles may be added from conventional volumetric feeders in a hammermill or from injectors on a paper making line.

One method for uniformly coating the fibers with a binder and adding the particles is shown in U.S. Pat. No. 5,064,689, which is incorporated herein by reference. However, the invention is not limited to any specific mechanism for combining the fiber, binder and particles.

Composite Absorbent Product

In accordance with the present invention, absorbent structures or articles may be made from the fibers, with the binder and adhered particles. These articles may be composite structures (e.g., made of plural materials). For example, the articles may have a core of plural types of fibers, or fiber layers, with or without covering materials. These products are capable of absorbing significant quantities of water and other fluids, such as urine and body fluids. Such products include, but are not limited to, disposable diapers, sanitary napkins, incontinent pads, towels and the like.

Figure 2:
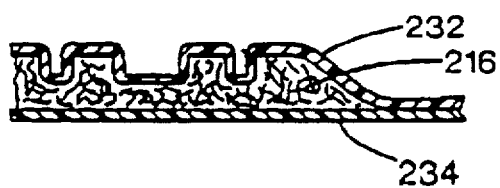
FIG. 2 represents a partial sectional view of the pad of FIG. 1.

As best shown in FIGS. 1 and 2, an absorbent towel or pad 200 may have a core 216 with a cover sheet 232 and a backing sheet 234. The core 216 may be comprised of fibers with the binders of the present invention and water soluble particulate materials, such as sodium bicarbonate particles secured to the fibers by the binder. The fibers that contain the binder may be blended with other fibers as well in the core. Cover sheet 232 is made of any suitable material, including liquid permeable, nonwoven materials, which will readily permit the passage of liquid through the cover sheet to the absorbent pad 216. The following list of liquid permeable materials is provided by way of example only: nonwoven sheets of polypropylene, rayon, nylon fibers, polyester fibers, and blends thereof. A specifically preferred cover sheet material for wipes is a 70% rayon/30% polyester blend having a basis weight of 21.5 grams/m$^2$, available from the Scott Paper Company.

The backing sheet 234 may be, but is not necessarily, made of a liquid impermeable material, including but not limited to, films of polyethylene, polypropylene and polyester and blends thereof along with nylon and polyvinyl chloride films. A specifically preferred backing sheet material is a polyethylene film from Dow Chemical Company.

FIGS. 1-2 illustrate an absorbent pad structure which may be formed from fibers of the present invention, whether or not they are blended with other fibers. FIGS. 1 and 2 represent an absorbent pad having a heat embossed screen pattern. Pads having no pattern may also be used. A pad having a cover sheet and a backing sheet may be formed, for example, by placing a square fiber piece cut from the sheet onto a corresponding precut backing sheet. A corresponding precut cover sheet is placed over the top of the fiber on the backing sheet. This assembly may then be adhesively bonded.

Figure 3:
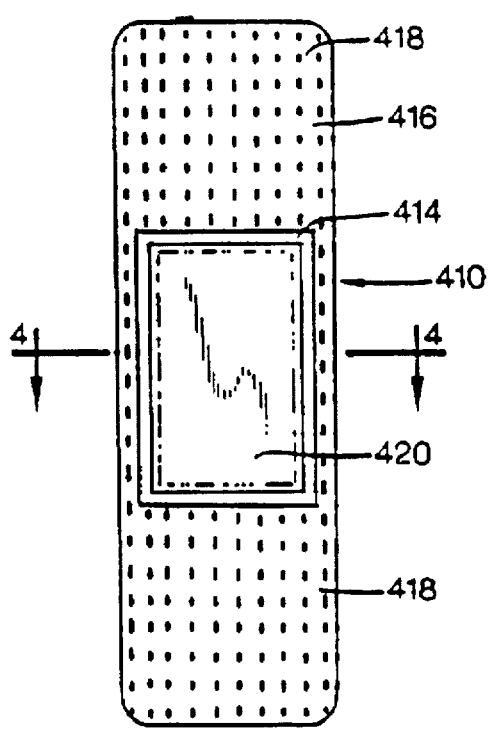
FIG. 3 illustrates a plan view of a bandage incorporating fibers of the present invention.
Figure 4:
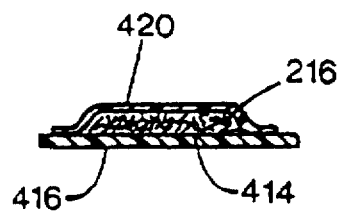
FIG. 4 is a sectional view of the bandage of FIG. 5, taken along line 4—4 of FIG. 3.

With reference to FIGS. 3-6, absorbent structures in the form of bandages or dressings are shown. In FIGS. 3 and 4, a bandage 410 for application to a wound to absorb blood and other bodily fluids is shown. An absorbent pad 216 (FIG. 4) is securely mounted to an exterior or pad mounting surface 414 of a backing strip 416. Any suitable mounting or securing means may be used to affix pad 216 to the surface 414 of the strip 416. However, it is preferable for surface 414 to be coated with an adhesive so that the pad 216 may be adhesively mounted in place. An exemplary adhesive is ethylene vinyl acetate adhesive. It is also desirable for the overall surface 418 of backing strip 416 to be coated with a conventional adhesive. Surface 418 is the surface which is affixed to the area of the skin surrounding the wound. Conventional "peel-back" tabs may be used to protect the adhesive coating and pad 216 until the bandage is to be applied. This type of backing strip is well known in the art.

The backing strip 416 may be of any known flexible material suitable for application to the skin. It is preferable for the strip 416 to be of a material which is impermeable to the passage of liquid so that fluid from a wound is contained by the bandage. However, the strip 416 may be apertured or otherwise breathable to permit air to reach the wound to promote the healing process. A specific example of a suitable backing strip 416 is a polyethylene film.

As in the other structures described, a variety of combinations of water soluble particles including antimicrobials as well as other particles may be used in such a bandage. Again, however, the particles are adhered securely in place when the particles have a hydrogen bonding or a coordinate covalent bonding functionality and the fibers to which these particles are bound have a hydrogen bonding functionality. The binder may be selected, for example, from the group consisting of a polypropylene glycol, a polypropylene glycol/polyethylene glycol copolymer, a polycarboxylic acid, such as polyacrylic acid, a poly(lactone)polyol, such as poly(caprolactone)diol, a polyamide, a polyamine, a polysulfonic acid, and combinations thereof, and the polymeric binder molecule has at least one hydrogen bonding functionality and at least one coordinate covalent bond forming functionality. Nonpolymeric binders would include organic binders such as glycerin, a glycerin monoester, a glycerin diester, a polyglycerol oligomer, propylene glycol, a polypropylene glycol oligomer, ascorbic acid, urea, glycine, pentaerythritol, a monosaccharide or a disaccharide, citric acid, tartaric acid, taurine, and urea derivatives such as DMDHEU. Suitable saccharides include glucose, sucrose, lactose, ribose, fructose, mannose, arabinose, and erythrose. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 216. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles with or without antimicrobial particles; and combinations of such fibers with untreated fibers and/or binder coated fibers without superabsorbent particles or antimicrobial particles. In addition, other particles, such as anticoagulants or hemostatics may be attached to the fibers. The absorbent pad 216 of bandage 410 may also include a cover sheet 420. Cover sheet 420 is typically made of any suitable material which will readily permit the passage of liquid through the cover sheet to the absorbent pad 216, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m$^2$ from Scott Paper Company.

Figure 5:
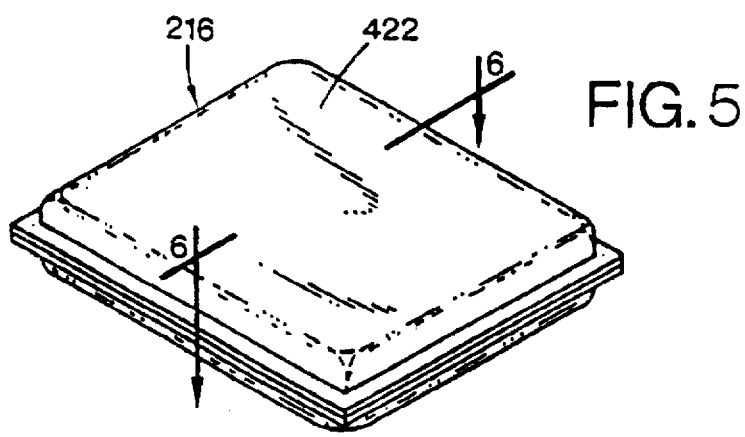
FIG. 5 is a perspective view of an absorbent structure of fibers of the present invention.
Figure 6:
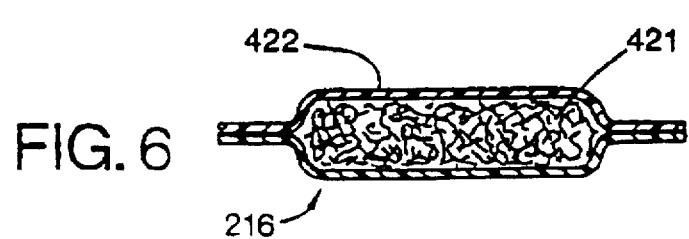
FIG. 6 is a cross-sectional view of the article or structure of FIG. 5, taken along line 6—6 of FIG. 5.

The dressing 216 shown in FIGS. 5 and 6 illustrates fibers 421 placed within an enclosure 422. Enclosure 422 has at least one liquid permeable surface through which fluid or liquid may pass to be absorbed by the fibers. The enclosure containing the loose fibers may be secured to the skin using adhesive tape, for example. Again, the fibers 421 preferably include antimicrobial particles attached to at least some of the fibers.

Figure 7:
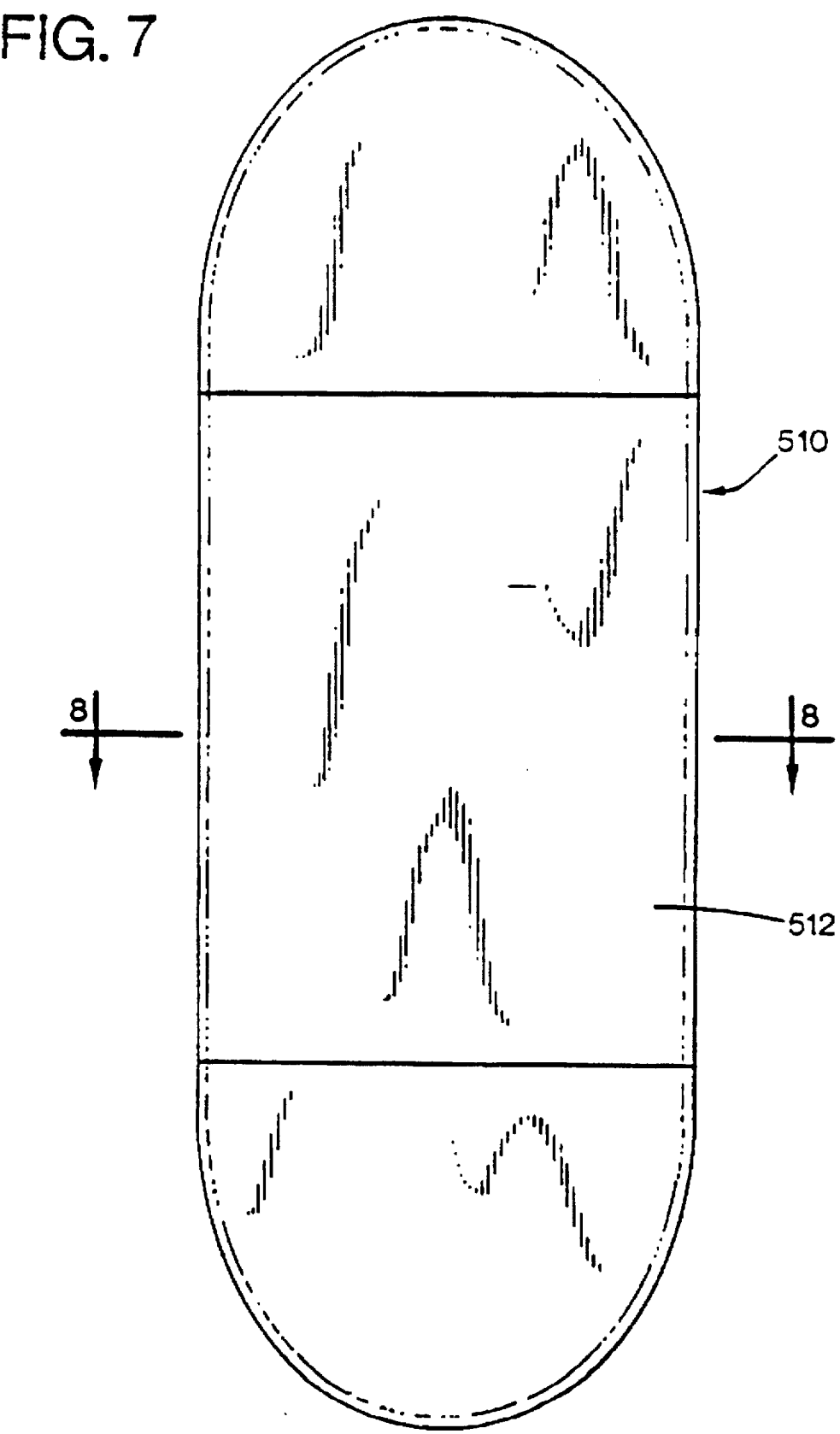
FIG. 7 is a plan view of a feminine hygiene appliance incorporating fibers of the present invention.

FIGS. 7 and 8 illustrate fibers of the present invention incorporated into a feminine hygiene appliance such as a feminine pad or tampon. In this case, the feminine pad 510 is illustrated as having a cover sheet 512. The loose fibers having adhered antimicrobial particles, which may alternatively be in the form of a pad, are included within the interior of the feminine appliance as indicated at 216 in FIG. 2. The cover 512 is preferably liquid permeable so that bodily fluids may reach the interior of the pad for purposes of absorption. The cover 512 may be wrapped around the core 216 (as indicated by edges 514, 515). A backing sheet 516, preferably of a liquid impermeable material, may be adhered to the edges 514, 515 at the underside of the core. An adhesive containing strip, such as indicated at 520, which may have a peelable or removable cover, may be mounted to the backing sheet 516 for use in adhering the pad, for example to a user's undergarment, during use.

FIGS. 9 and 10 illustrate a conventional disposable diaper 550 with a core 552 which is comprised of fibers of the present invention with adhered particulate materials. These particulate materials may be confined to a target zone (for example, the front portion of a diaper indicated at 556) or of a heavier concentration in the target zone. This can be accomplished, for example, by airlaying fibers of the present invention in such a zone. Also, the core may be activated by melting the binder or moistening the target zone with a liquid in which the particles are not significantly soluble. The superabsorbent particles may be sprinkled on or otherwise applied to this wetted zone. As the zone dries, the particles are adhered in place.

Densification

The products such as described above, as well as webs of the fibers of the present invention, can also be densified by external application of pressure to the web. The web of can be densified by passing it through a set of calendar rolls set at 60 and 90 pli (pounds per linear inch, as in a calendar press) respectively to yield sheets with increased densities. Densification may alternatively be provided by compaction rolls or presses. The present inventors have found that densification is facilitated in the products treated with the binders of the present invention. Products that are treated with these binders require less heat and pressure than untreated fibers to densify to a given density. Densification is preferably performed to produce a product that has a density of about 0.1 to 0.7 g/cc, more preferably 0.1 to 0.3 g/cc.

Particulate Binding

FIG. 11 shows an isolated, enlarged cellulose fiber 600 with particles 602 bound to it by a binder of the present invention. This drawing illustrates an example of the particles retaining its discrete particulate form following binding to the fibers. Some particle to particle fusion may occur in accordance with this invention, but maintenance of a discrete particulate form excludes formation of a completely confluent film in which the particles lose their particulate identity. The shown fiber 600 is elongated, and has an aspect ratio (ratio of length to width) of about 10:1.

FIG. 12 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

As can be seen from FIGS. 11-12 (and FIGS. 13-14 discussed below), the particles are not encapsulated by the binders. The particles and fibers of the present invention are not encapsulated with the binder. Moreover, the binder does not agglomerate the fibers together, and in many embodiments does not bind fibers to each other. Discrete individual particles retain their identity on the surface of the fibers, instead of being subsumed in a thermoplastic encasement around the fiber and particle.

EXAMPLE X

An electron photomicrograph of oxalic acid particles bound to cellulose fibers with a glycerin binder is shown in FIG. 13. The bound oxalic acid is near the center of the photograph. The binder does not encapsulate with the fiber or the particle.

FIG. 14 is an SEM illustrating a particle of aluminum sulfate (alum) bound to a cellulose fiber with a glycerin binder. The alum particle is seen at the center of the photograph, and the particle retains its individual particulate form. The particles do not form a confluent mass lacking particulate identity. Moreover, the particles are not encapsulated by the binder.

Fiber Mixtures

The fibers of the present invention, such as fiber 600, can be mixed with other types of fibers, such as that disclosed in U.S. Pat. No. 5,057,166 which is incorporated herein by reference in its entirety. The latex coated fibers of that patent can be mixed with the fibers of the present invention to produce an absorbent product that has characteristics of both types of fibers.

Additional Binder Characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidifying into a brittle film. The binders of the present invention, in contrast, are capable of functioning as a binder after solidifying into a rigid crystalline material. Even the binders of the present invention that do not rigidify into a solid (such as glycerin and polyglycerols) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they produce a tacky material that is difficult to process with conventional equipment. The polysaccharide polymers are also excluded from non-polymeric embodiments of the binder of the present invention. The saccharide and disaccharide embodiments of the non-polymeric binder of the present invention, have greater mobility in the product, which may make such binders more effective. Moreover, the non-polymeric saccharides such as monosaccharides and disaccharides, lack the high viscosity and tacky-adhesive physical properties of polysaccharides such as corn syrup and honey. The non-polymeric saccharides of the present invention may be solids, which avoid the viscosity and handling problems associated with polymers.

As used in this application, a particle that is soluble in water means that at least 10 g of the particle will dissolve in 300 ml of water at 25° C. A particle that is sparingly soluble in the binder will completely dissolve no more than about 5 g of the particle in 300 ml of the binder at 25° C.

Some of the binders of the present invention also are water soluble. As used herein, a "soluble" binder or "a binder that is soluble in water" means that at least 10 g of the binder will substantially completely dissolve in about 300 ml water at 25° C.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. Fibers with adhered particles, comprising:
    particles with a hydrogen bonding or a coordinate covalent bonding functionality, the particles being water soluble;
    fibers that have hydrogen bonding functional sites; and
    a binder on the fibers, the binder having a volatility less than water, the binder comprising binder molecules, the binder molecules having at least one functional group that is capable of forming a hydrogen bond with the fibers, and at least one functional group that is capable of forming a hydrogen bond or coordinate covalent bond with the particles, wherein the particles are sparingly soluble in the binder, and the binder being present in an amount of at least 1 percent by weight of the fibers and which is sufficient to bind a substantial portion of the particles to the fibers primarily by a hydrogen bond or coordinate covalent bond.

2. The fibers of claim 1 wherein the binder is selected from the group consisting of (a) a polymeric binder with repeating units wherein the binder has at least one functional group capable of forming a hydrogen bond or a coordinate covalent bond with the particles, and at least one functional group capable of forming a hydrogen bond with the fibers; (b) a non-polymeric organic binder with a functional group capable of forming a hydrogen bond or a coordinate covalent bond with the particles, and a functional group capable of forming a hydrogen bond with the fibers; and (c) combinations of such polymeric and non-polymeric binders with each other or with other binders wherein the binders do not react to block the functional groups.

3. The fibers of claim 1 wherein the binder is a polymeric binder selected from the group consisting of a polyglycol, a poly(lactone) polyol, a polycarboxylic acid, a polycarboxylate, a polysulfonic acid, a polysulfonate, a polyamide, a polyamine, and copolymers thereof.

4. The fibers of claim 1 wherein the binder is selected from the group consisting of polycarboxylic acids, polyamides and polyamines, and copolymers thereof.

5. The fibers of claim 1 wherein the binder is a non-polymeric organic binder which has functional groups selected from the group consisting of a carboxyl, a carboxylate, a carbonyl, a hydroxyl, a sulfonic acid, a sulfonate, a phosphate, a phosphoric acid, an alcohol, an amide, an amine, and mixtures or combinations thereof, and wherein there are at least two functionalities on the molecule selected from this group, and the two functionalities are the same or different.

6. The fibers of claim 1 wherein the binder is a non-polymeric organic binder selected from the group consisting of a carboxylic acid, a hydroxy acid, an amino acid, a carboxy amide, a polyol, and an amino alcohol.

7. The fibers of claim 1 wherein the binder is a non-polymeric organic binder selected from the group consisting of glycerin, a glycerin monoester, a glycerin diester, propylene glycol, glyoxal, ascorbic acid, urea, glycine, pentaerythritol, a monosaccharide, a disaccharide, citric acid, tartaric acid, taurine, dipropylene glycol, an urea derivative, and combinations thereof.

8. An absorbent article comprising the fibers of claim 1.

9. The absorbent article of claim 8, wherein the fibers are cellulose fibers and the absorbent article is selected from the group consisting of a feminine hygiene appliance, a disposable diaper, and a bandage.

10. The fibers of claim 7 in which the binder is not a saccharide.

11. The fibers of claim 7 in which the binder is capable of forming a crystalline solid upon drying.

12. A fiber product, comprising:
fibers that have hydrogen-bonding functional sites;
a binder having a volatility less than water, the binder comprising binder molecules, the binder molecules having a first functional group that is capable of forming a hydrogen bond with the fibers, and a second functional group that is capable of forming a hydrogen bond or a coordinate covalent bond; and
particles that have a hydrogen bonding or a coordinate covalent bonding functionality wherein the particles are soluble in water and sparingly soluble in the binder, a substantial portion of the particles being bound in particulate form to the fibers primarily by a hydrogen bond or a coordinate covalent bond.

13. The product according to claim 12 wherein the fiber product is an absorbent product.

14. A fiber product comprising:
individualized fibers that have hydrogen bonding functional sites; and
a binder having a volatility less than water, the binder comprising binder molecules, the binder molecules having a first functional group that is capable of forming a hydrogen bond with the fibers, and a second functional group that is capable of forming a hydrogen bond or a coordinate covalent bond with particles that are soluble in water and sparingly soluble in the binder, the binder selected from polymeric binders selected from the group consisting of polyacrylic acid, a poly(lactone) polyol, a polysulfonic acid, a polysulfonate, a polyamide, and copolymers thereof, nonpolymeric binders, and combinations of the polymeric and non-polymeric binders with each other or with other binders wherein the binders do not react to block the functional groups.

15. The fiber product of claim 14, wherein the binder is present in an amount of at least 1% by weight of the fibers and which is sufficient to bind a substantial portion of the particles to the fibers primarily by a hydrogen bond or a coordinate covalent bond.

16. The fiber product of claim 14, wherein the fibers comprise wood pulp fibers.

17. The fibers of claim 14, wherein the nonpolymeric binder has functional groups selected from the group consisting of a carboxyl, a carboxylate, a carbonyl, a hydroxyl, a sulfonic acid, a sulfonate, a phosphoric acid, a phosphate, an alcohol, an amide, an amine, and mixtures and combinations thereof, and wherein there are at least two functionalities on the molecule selected from this group, and the two functionalities are the same or different.

18. The fiber product of claim 14, wherein the nonpolymeric binder is selected from the group consisting of an amino acid, an amide and an amine.

19. The fiber product of claim 14, wherein the nonpolymeric binder is selected from the group consisting of a carboxylic acid, a hydroxy acid, an amino acid, and an amide.

20. The fiber product of claim 17, wherein the nonpolymeric binder includes more than one amine functionality.

21. The fiber product of claim 17, wherein the nonpolymeric binder is selected from the group consisting of a hydroxyamide and an organic binder that includes more than one amide functionality.

22. The fiber product of claim 17, wherein the nonpolymeric binder is selected from the group consisting of glycerin, a glycerin monoester, a glycerin diester, propylene glycol, glyoxal, ascorbic acid, urea, glycine, pentaerythritol, a monosaccharide, a disaccharide, citric acid, tartaric acid, taurine, urea derivatives, and combinations thereof.

23. Fibers with adhered particles produced by the method comprising:
providing fibrous material comprising fibers that have hydrogen bonding functional sites;
applying a binder to the fibers, the binder having a volatility less than water, the binder comprising binder molecules, the binder molecules having at least one functional group that is capable of forming a hydrogen bond with the fibers, and at least one functional group that is capable of forming a hydrogen bond or a coordinate covalent bond with particles that have a hydrogen bonding or a coordinate covalent bonding functionality; and
adding the particles with a hydrogen bonding or a coordinate covalent bonding functionality to the fibers wherein the particles are soluble in water and sparingly soluble in the binder, whereby a substantial portion of the particles are bound in particulate form to the fibers primarily by a hydrogen bond or a coordinate covalent bond.

24. The fibers of claim 23, wherein the binder is selected from the group consisting of (a) a polymeric binder with repeating units, the binder having a functional group capable of forming a hydrogen bond or a coordinate covalent bond with the particles, and a functional group capable of forming a hydrogen bond with the fibers; (b) a non-polymeric organic binder with a functional group capable of forming a hydrogen bond or a coordinate covalent bond with the particles, and a functional group capable of forming a hydrogen bond with the fibers; and (c) combinations of such polymeric and nonpolymeric binders with each other or with other binders wherein the binders do not react to block the functional groups.

25. The fibers of claim 24, wherein the particles have a solubility in water of at least 10 g in 300 ml water at 25° C., and a solubility in the binder of no more than about 5 g in 300 ml of the binder at 25° C.

26. The fibers of claim 24, wherein the method further comprises the step of activating the binder on the fibers from an inactive state.

27. Fibers with adhered particles, comprising:

particles with a hydrogen bonding or a coordinate covalent bonding functionality, the particles being water soluble;

fibers that have hydrogen bonding functional sites; and a binder on the fibers, the binder having a volatility less than water, the binder comprising binder molecules, the binder molecules having at least one functional group that is capable of forming a hydrogen bond with the fibers, and at least one functional group that is capable of forming a hydrogen bond or a coordinate covalent bond with the particles, wherein the particles are soluble in the binder, the binder being present in an amount of at least one percent by weight of the fiber and which is sufficient to bind a substantial portion of the particles to the fibers primarily by a hydrogen bond or coordinate covalent bond.

28. An absorbent article comprised of the fibers of claim 23, 24, 25 or 26.

29. The fibers of claim 2, wherein the non-polymeric organic binder has functional groups that are selected from the group consisting of a sulfonic acid, a sulfonate, a phosphoric acid, a phosphate, an amide, an amine, and combinations thereof.

30. The fiber product of claim 14, wherein the non-polymeric binder has functional groups selected from the group consisting of a sulfonic acid, a sulfonate, a phosphoric acid, a phosphate, an amide, an amine, and combinations thereof.

31. The fibers of claim 24, wherein the non-polymeric organic binder has functional groups that are selected from the group consisting of a sulfonic acid, a sulfonate, a phosphoric acid, a phosphate, an amide, an amine, and combinations thereof.

32. The fibers of claim 27, wherein the binder has functional groups that are selected from the group consisting of a sulfonic acid, a sulfonate, a phosphoric acid, a phosphate, an amide, an amine, and combinations thereof.

* * * * *